United States Patent
Anderson et al.

(10) Patent No.: US 8,728,829 B2
(45) Date of Patent: May 20, 2014

(54) COMPOSITIONS FOR BINDING TO ASSAY SUBSTRATA AND METHODS OF USING

(75) Inventors: David M. Anderson, Ashland, VA (US); Richard G. Saul, Ashland, VA (US)

(73) Assignee: Lyotropic Therapeutics, Inc., Ashland, VA (US)

( * ) Notice: Subject to any disclaimer, the term of this patent is extended or adjusted under 35 U.S.C. 154(b) by 869 days.

(21) Appl. No.: 12/905,653

(22) Filed: Oct. 15, 2010

(65) Prior Publication Data

US 2011/0027813 A1 Feb. 3, 2011

Related U.S. Application Data

(62) Division of application No. 11/296,696, filed on Dec. 8, 2005, now Pat. No. 7,838,307.

(60) Provisional application No. 60/634,080, filed on Dec. 8, 2004.

(51) Int. Cl.
 *G01N 33/551* (2006.01)

(52) U.S. Cl.
 USPC ............ 436/524; 436/518; 436/501; 435/7.1; 435/283.1; 435/287.1; 435/287.2; 435/288.7

(58) Field of Classification Search
 USPC ................ 436/518, 501, 524; 435/7.1, 283.1, 435/287.1, 287.2, 288.7
 See application file for complete search history.

(56) References Cited

U.S. PATENT DOCUMENTS

| | | | |
|---|---|---|---|
| 4,966,839 A | 10/1990 | Kaspar | |
| 5,561,097 A | 10/1996 | Gleason et al. | |
| 5,603,868 A | 2/1997 | Wang et al. | |
| 5,808,300 A | 9/1998 | Caprioli | |
| 6,133,436 A | 10/2000 | Koster et al. | |
| 6,482,517 B1 | 11/2002 | Anderson | |
| 6,579,719 B1 | 6/2003 | Hutchens et al. | |
| 6,630,358 B1 | 10/2003 | Wagner et al. | |
| 6,638,621 B2 | 10/2003 | Anderson | |
| 6,797,463 B2 * | 9/2004 | Abbott et al. | 435/5 |
| 2002/0146745 A1 | 10/2002 | Natan et al. | |
| 2003/0017464 A1 | 1/2003 | Pohl | |
| 2003/0232340 A1 | 12/2003 | Anderson | |
| 2004/0241436 A1 | 12/2004 | Hsieh et al. | |
| 2005/0221271 A1 * | 10/2005 | Murphy et al. | 435/4 |

OTHER PUBLICATIONS

International Search Report issued on Jul. 8, 2008 for the related PCT application, pp. 1 to 15.

* cited by examiner

*Primary Examiner* — Melanie Y Brown
(74) *Attorney, Agent, or Firm* — Whitham, Curtis, Christofferson & Cook, P.C.

(57) ABSTRACT

Compositions and methods for binding to assay substrata in a stable and protective manner, thereby enhancing assay performance, are provided. The compositions comprise lyotropic materials (for example, lyotropic liquid and/or liquid crystalline materials) and may contain macromolecular standards, markers or capture compounds. The compositions are capable of binding to assay substrata such as that of chips that are employed for MALDI and SELDI mass spectroscopy analyzes and plates that are used for ELISA type assays.

13 Claims, 6 Drawing Sheets

COMPOSITIONS FOR BINDING TO ASSAY SUBSTRATA AND METHODS OF USING

The present application is a divisional application of U.S. patent application Ser. No. 11/296,696 filed Dec. 8, 2005 and claims benefit of U.S. provisional patent application 60/634,080 filed Dec. 12, 2004, the complete contents of which is hereby incorporated by reference.

BACKGROUND OF THE INVENTION

1. Field of the Invention

The invention generally relates to compositions and methods for binding to assay substrata, including compositions containing and methods involving proteins, peptides, nucleic acids and other compounds of importance in biochemical assays, for binding to substrata in a stable, protective, and robust manner. In particular, the invention provides compositions of lyotropic liquid and/or, preferably, liquid crystalline materials capable of binding to assay substrata, including compositions containing assay-associated compounds, particularly biomacromolecules. The biomolecules of interest include molecular weight standards, disease markers, and capture compounds such as antibodies, antigens, receptors, ligands, lectins, chimeras, complementary nucleic acids, antisense compounds, avidin, etc. The lyotropic materials are capable of binding to assay substrata, such as that of the chips that are employed for Matrix-Assisted lased Desorption Ionization (MALDI) and Surface-Enhanced Laser Desorption Ionization (SELDI) mass spectroscopy analyses, providing a stable, protective environment for the compounds and a robust means for deposition on the chip with resulting improvement in signal strength and reproducibility. They are also capable of binding to substrata used in more traditional types of protein assays, such as Enzyme-Linked ImmunoSorbent Assays (ELISAs), for effective deposition of reagents and markers, as well as for blocking non-specific binding (NSB).

2. Background of the Invention

Assays based on mass spectroscopy techniques, such as Matrix-Assisted Laser Desorption Ionization (MALDI) and Surface-Enhanced Laser Desorption Ionization (SELDI) are gaining importance in a number of analytical applications, including early detection of cancer, infectious diseases, and other pathological conditions. In mass spec as well as in other assay methods, it can be important to have one or more standards present, added ("spiked") to the sample fluid, in order to provide for calibration of both the charge/mass ratio and the intensity. However, in such applications, the presence of compounds in biological fluids that can degrade proteins, peptides and other standards is in many cases inevitable; such compounds include proteases, lysozyme, trypsin, nucleases, etc. Facilitating the use of simple, relatively inexpensive, and well-studied standards such as peptides and proteins calls for a method to protect the standard molecule from degradative enzymes and other conditions or compounds, and for accomplishing a high degree of substrate binding for signal enhancement.

In addition, SELDI is a mass spec technique that, through the use of sample substrata with specially tailored surface chemistries, can be of tremendous advantage in selecting desired standards and markers as well as increasing their signal:noise ratios, but is currently not used to full advantage. As an example, in the case where two standard molecules are used in order to provide better calibration, the variance in binding between the two (or more) molecules on SELDI chips, the run-to-run variability of the peak positions and intensities, and variability in the SELDI chips themselves, confounds the calibration of peak positions (m/z ratios) and intensities. This is particularly true in cases where imprecision in calibration of m/z ratios leads to improper integration of peaks.

In the art of laser-desorption mass spectrometry a number of substrates have been developed for selective adsorption of targeted molecules of importance in, e.g., biomedical assays. U.S. Pat. No. 6,579,719 for example describes methods for applying charged and hydrophobic-interaction surfaces for selective capture of biomarkers in the context of laser-desorption mass spectrometry.

In solid-phase assays, there is a need for protein-friendly, even biomimetic, materials and methods for hosting capture molecules and other assay-associated proteins, in such a way that the analyte molecules are captured efficiently and can be brought down to the substrate with high affinity. There is a fundamental challenge in this endeavor which has placed limitations on the quantification, specificity, and ease of use of current methods, and this challenge is very pronounced in certain cases, such as the case of receptor-based assays: namely, by definition, solid-phase assays involve solid-liquid interfaces that tend to denature sensitive proteins such as receptors, as well as other membrane-associated proteins. Indeed, it is well known that membrane-associated proteins tend to denature or flocculate over time even in simple aqueous (buffered) solution, and the more mature techniques in the study of these compounds ensure that at least some lipid is retained in the preparations used in analyses. The analysis of ligand-receptor interactions is of central importance in the screening of potential pharmaceutical actives, and yet there remains a major unsolved problem, at the time of this writing, of how to design a material that will preserve the natural functionality and characteristics of receptor proteins and other functional biomacromolecules and, at the same time, exhibit desired binding to useful substrata. Broadly speaking, a solid surface is an excellent means by which to concentrate species which, in solution or suspension, would be so dilute as to be difficult to quantify, yet the same surface can wreak havoc with delicate proteins such as receptors. Even glycolipid receptors, such as bacterial adhesin receptors, have been shown to yield erroneous, non-physiologic binding selectivity results when used in traditional solid-phase assays, due to improper presentation of the saccharide head groups when the lipid is adsorbed to a solid surface. There is a clear need, particularly in the pharmaceutical industry, for materials that can provide a near-physiologic conformation and presentation of membrane proteins and receptors, preferably with access to both binding and active sites, yielding a degree of fidelity obtainable perhaps only with whole cell-based assays but in a simpler and more controlled system.

Regulatory feedback can alter receptor-based physiological responses, which are further contingent on interactions between different hormonal or signaling systems, and so it is important to interpret, e.g., pharmaceutical screening studies in the context of biochemical data reflecting direct receptor effects of drugs, in purified systems free from extraneous components. Furthermore the need for whole, intact receptor molecules hosted in a physiologic milieu is crucial in view of allosteric effects, competitive binding, multisite binding, desensitization, and other effects that quantitatively and even qualitatively modify binding. Allosteric effects, involving the global protein, which drive signal transduction, are in many receptors driven by the lower free energy associated with binding site/ligand interaction after binding-induced conformational changes; thus, in the absence of the entire protein and associated allosteric effects, studies of competitive binding can be qualitatively incorrect. In addition, with certain multisite receptors, it is known that the natural ligand and exogenous agonists/antagonists can bind to different sites, and so an assay based on a partially expressed protein exhibiting only the natural ligand binding site would yield false negatives with exogenous compounds, and the opportunity afforded by the new potential drug might well be missed. Similarly, in receptors such as the 5-HT-2c receptor, where the binding site involves a transmembrane domain, as well as in cases where the site is at the membrane/water interface or (as in the n-acetylcholine receptor) at the interface between two subunits, it would be erroneous to work only with a partially expressed protein representing a putative binding site. Discrimination between agonist and antagonist binding sites will clearly require intact receptor, and even such events as dimerization of the EGF receptor, which has a strong effect on binding affinity, apparently requires intact receptors, as receptor-related molecules such as the secreted binding domain and gp74v-erbB do not give evidence of dimerization. In view of these facts, there is a need to improve drug-screening assays by satisfying the need for a receptor with its allosteric regulatory mechanism intact, and with proper presentation and accessibility of binding site(s).

Liposomes have been used in conjunction with various biochemical assays, but suffer from instabilities, leakage, opsonization-related problems, incompatibilities with many proteins including membrane-associated proteins, and generally, greatly restricted access to the compounds they encapsulate. Concerning protein incompatibilities, even insulin has been shown to induce leakage of DPPC liposomes through bilayer interactions [Xian-rong et al., Acta Pharm. Sinica (2000) 35(12):924]. These limitations can preclude their use as carriers for bioactive and capture molecules, or at least require tethering of these compounds via laborious and/or expensive conjugation procedures. Use of liposomes in diagnostics is largely limited to the use of high-transition temperature lipid bilayers because of their resistance to instability, rancidification, and opsonization, at least in the case of ready-to-use products. Obviously crystalline materials are essentially non-functional as solvents, and thus integral proteins cannot be incorporated. This in turn largely limits the use of liposomes to the encapsulation of compounds inside the aqueous interior of a rigid liposome, leaving the compound inaccessible to the crucial intermolecular interactions that are central to, for example, immunoassays. Furthermore, the spherical shape of liposomes is simply not conducive to intimate substrate contact.

In summary, it would be a boon for researchers, clinical chemists, pharmaceutical scientists and others dealing with bioassays to have available compositions (e.g. carrier particles) whereby assay-associated molecules could be sequestered, protected, and subsequently deposited reliably on selected substrata.

Simple micelles and microemulsion droplets are not well suited as carrier particles for helping to bind macromolecules to substrata, and also poorly suited for providing a protective encapsulation. Both are very labile, not to be viewed as having any sort of permanence, and in the current theory are viewed as very rapidly exchanging material with each other, with any surfaces present, and with the aqueous domains. And if an ionic interaction between surfactant and substrate were sufficiently strong, the likely result would not be micelles or microemulsion droplets adsorbed to the substrate, but rather individual molecules adsorbed (to form a monolayer, or perhaps multilayer).

In addition, one of the commonly held beliefs by those practiced in the art of MALDI has been that the presence of lipids in samples, suppresses ionization and therefore is detrimental to MALDI analysis. Further, since SELDI is a form of MALDI, one might have expected that the addition of lipids to samples would have caused the expected ion suppression. This belief obviously has taught away from the use of lipid-based materials in connection with MALDI and SELDI.

The prior art has thus far failed to provide compositions, and methods for their use, whereby standard molecules can be bound to assay substrata, particularly in a manner whereby the standards are protected and stabilized. Similarly, materials for hosting biospecific capture molecules and other assay-associated compounds, and for sequestering analytes from solution, have suffered from a non-physiologic nature, laborious conjugation procedures, sub-optimal substrate binding, limiting instabilities, poor presentation of binding groups, and/or obstructions to key molecular interactions.

SUMMARY OF THE INVENTION

The present invention provides compositions and methods for binding to assay substrata, including compositions containing biomolecules such as standards, disease markers, and capture compounds. The compositions can be bound to assay substrata, such as the surface of an assay chip or other support. The compositions comprise lyotropic materials (such as lyotropic liquids or liquid crystalline materials, and in particular cubic phase materials), and the standards and/or capture compounds are contained within the lyotropic material. The invention is based on the discovery that such compositions stably bind to surfaces such as those used for the substrata of many assay systems, e.g. to the surface of SELDI-MS chips and ELISA plates. Not only do the compositions bind to such surfaces, they do so in a manner that retains the standard or capture (and captured) molecule(s) within the protective, stable environment of the lyotropic material. As a result, the standards and capture compounds are not exposed to the many potentially harmful substances that are present in biological samples nor to the denaturing effects of certain surfaces or environments, their integrity is preserved, and the accuracy of measurements relying on these compounds is enhanced. Surprisingly, it has also been found that at least some of these compositions and methods substantially or even dramatically reduce the run-to-run variability of laser-desorption mass spec measurements and increase signal: noise ratios.

One aspect of the instant invention is the binding of lyotropic liquid or, more preferably, liquid crystalline material, to a substrate so as to coat (partially or fully) the substrate with either a collection of particles or a film, which in turn may or may not be coated. In some cases, the lyotropic material and the substrate will be chosen together, in tandem, so as to yield the desired binding. This can be accomplished by judicious use of one or more of the following three general approaches:

A) coating: particles of lyotropic material are at least partially covered with a coating material that is selected so as to bind to the substrate;

B) compound in the lyotropic material: the lyotropic material is chosen so as to incorporate one or more compounds that promote binding of the material to the substrate; most preferably these compounds are bilayer-associated; less preferably, a non-bilayer-associated compound in the lyotropic material is retained in the material by a gelation step that is carried out within the lyotropic material;

C) hydrophobic interaction: the lyotropic material and substrate are selected in such a way that a hydrophobic interaction between the two promotes binding.

It is an exemplary embodiment of this invention to provide compositions incorporating proteins and/or peptides, dendrimers or other macromolecules, wherein said compositions bind to MALDI and SELDI substrata and other assay substrata, including especially compositions comprising microparticles and coated microparticles of nanostructured liquid and liquid crystalline phase materials. Such compositions can provide protection of the standard molecule by encapsulation, or by incorporation in a matrix that is not easily penetrated by degradative enzymes. They can be used to standardize charge:mass ratios, as well as intensities, in MALDI and SELDI measurements, thereby yielding greater accuracy and enhanced capabilities. Virtually any number of peptides or proteins, for standardization or specific capture, can be incorporated into a system of particles with much greater control over the resulting molar ratios between the various proteins on the assay chip, since entire particles can be bound to the chip along with their full payload. In one embodiment of the invention, capture molecules (e.g., antibodies, receptors, etc.) are incorporated in or at the surface of such lyotropic microparticles, particularly those based on reversed liquid crystalline phase materials and most preferably on reversed cubic phase materials, allowing specific capture of important analyte molecules. This attribute can be coupled with the strongly substrate-binding property of the compositions described herein, to yield a synergistic combination of selective analyte capture and substrate deposition. In yet another embodiment, the compositions can be used as blocking agents in immunoassays and related assay methods, to limit non-specific binding (NSB) and increase sensitivity and accuracy.

In preferred embodiments, such a composition includes one or more particles comprising a matrix consisting essentially of a nanostructured liquid or liquid crystalline phase material, most preferably a reversed lyotropic liquid crystalline material. Such a particle achieves its binding to a selected substrate by virtue of a preselected surface chemistry, which can be, for example, cationic charge, anionic charge, hydrophobicity, chelating groups, hydrogen bonding groups, avidin/biotinylation, and the presence of antibodies, lectins, nucleic acids, receptors, chimera, and other biospecific targets at or near the surface of the particle. In the preferred embodiments, this surface chemistry can be attained either on a coated particle of nanostructured liquid or liquid crystalline phase interior, or at the surface of an uncoated particle most preferably of a reversed liquid crystalline phase. The particles can likewise comprise chemical moieties that bind to specific antigens or other molecules to be captured, such as specific antigens in the body that are most preferably markers of disease. Thus, capture molecules such as antibodies and the associated capture-promoting interactions (e.g., antigen-antibody interaction) can play two rather different roles in these particles: as a means to sequester analyte molecules from solution prior to substrate binding, and as a means to achieve binding to a substrate incorporating the appropriate compound. A particularly instructive example of this, dual functionality is the following: a lyotropic liquid crystalline particle containing a first antibody to an analyte binds the analyte from solution (e.g., from diluted serum), and the particle in turn binds to a secondary antibody to the same antigen immobilized at the substrate surface.

It is another exemplary embodiment of this invention to provide methods for producing and using such particles. In particular, a preferred method of using such particles (illustrated schematically in FIG. 1) comprises addition of the particles containing one or more of said compounds to a sample of biological material, such as serum, incubation of the now-spiked serum with the appropriate SELDI substrate, washing away of non-attached material, and subsequently applying a laser energy-absorbing matrix and performing SELDI-MS as per normal operation; the mass spectrometry peaks recorded from the encapsulated macromolecules then provide an accurate standardization of the charge:mass ratio (known from the MW of the macromolecule, which is selected to be readily distinguishable from expected endogenous macromolecules, and exhibiting sharp, well-defined MS peaks), and of the intensities provided that intensities, from the encapsulated marker macromolecules are reproducible to sufficient accuracy. Preferably, compositions that comprise everything needed to make this procedure work in a turn-key fashion are used. Preferably, the particles are in a stabilized form that is compatible with the biological material, and contain one or more macromolecules (e.g. peptides, proteins, etc.) such that the mass spec signal intensity from the use of the composition is significantly greater than the signal which would be obtained with the same amount of macromolecule in the absence of the particles, for example with an aqueous solution of the macromolecule. Certain preferred particles of the invention have the property that they comprise capture moieties, such as antibodies and the like, and will carry captured molecules down to the desired surface upon binding to that surface, be it a SELDI substrate (illustrated schematically in FIG. 2b) or other assay substrate (FIG. 2a); thus the method of using comprises contacting the particles with a biological solution possibly containing the molecule or antigen to be captured, and at some point before, after, or during that time, contacting the particles or a dispersion thereof with the substrate of interest.

In another exemplary embodiment (illustrated in FIG. 3), certain preferred, particles enhance surface binding of a molecule or antigen to be studied in a sample even without the incorporation of a specific capture molecule in the particles, by contacting the particles with a biological solution containing sample and at some point before, after, or during that time, contacting the particles or a dispersion thereof and sample solution with the substrate. (FIG. 3). This may enhance matrix deposition on the substrate in assays such as MALDI and SELDI, for example by inducing a much finer and more uniform deposition of the energy-absorbing matrix and/or a more intimate association between it and the analyte material.

In yet another exemplary embodiment (schematically illustrated in FIG. 4), similar particles are applied to a substrate such as an ELISA plate in order to block areas where non-specific binding can otherwise occur.

The invention provides a calibration method for use in assays, comprising the steps of: 1) applying to a surface of a substrate a composition comprising lyotropic liquid or liquid crystalline material in which is incorporated one or more marker molecules, said composition binding to the surface of said substrate; and 2) using data which is derived from said one or more marker molecules as a calibration standard. In one embodiment, the composition is provided in the form of particles, which may be coated or uncoated. Two different marker molecules may be present in two different particles, or in the same particle. In one embodiment, the one or more marker molecules are proteins or peptides, for example, proteins and peptides that are applicable to cancer detection. Relevant assays include ELISA assays, MALDI assays and SELDI assays. In some embodiments, the binding may be via, for example, hydrogen bonding or ionic bonding. In one embodiment, the substrate is inorganic. In some embodiments, the composition is provided in the form of a film. In some embodiments, the lyotropic liquid or liquid crystalline material is cubic phase.

The invention further provides a composition or kit used for calibration in an assay. The composition or kit comprises 1) at least a first particle formed from a lyotropic liquid or liquid crystalline material and having a first protein or peptide marker molecule; and at least a second particle formed from a lyotropic liquid or liquid crystalline material and having a second protein or peptide marker molecule, wherein said second protein or peptide marker molecule is different from said first protein or peptide marker molecule, and wherein each of said at least a first particle and said at least a second particle bind directly to a surface of a substrate suitable for use in an assay. In some embodiments, the at least a first particle and said at least a second particle are coated; in others, they are uncoated. The at least a first particle and said at least a second particle may be combined in a single container. Alternatively, they may be stored in separate containers. In one embodiment, the substrate is used in an assay such as, for example, an ELISA, MALDI, or SELDI assay.

The invention further provides a method of performing an assay for a molecule of interest in a sample. The method comprises the steps of 1) combining a sample with a composition of lyotropic liquid or liquid crystalline material; 2) binding said composition of lyotropic liquid or liquid crystalline material to a substrate; and 3) measuring for one or more molecules of interest on said substrate. In some embodiments, the measuring step is performed qualitatively. In other embodiments, the measuring step is performed quantitatively. The step of binding may be performed by said composition bonding directly to said substrate, e.g. by hydrogen bonding or ionic bonding. In some embodiments, sample is a liquid medium such as blood, serum, or urine. In one embodiment, the composition is combined with said sample in said combining step in the form of a plurality of particles. In another embodiment, at least two of said plurality of particles include different capture molecules. The measuring step of the method may be performed in an assay such as, for example, ELISA, MALDI or SELDI. In a preferred embodiment, the lyotropic liquid or liquid crystalline material is cubic phase. The molecule of interest may be a cancer marker.

The invention further provides a method of performing an assay, which comprises the steps of 1) combining a sample with a composition of lyotropic liquid or liquid crystalline material which has incorporated therein one or more capture molecules; 2) allowing one or more analyte molecules in said sample to bind with said one or more capture molecules in said composition of lyotropic liquid or liquid crystalline material; 3) binding said composition of lyotropic liquid or liquid crystalline material to a substrate; and 4) measuring the analyte molecules bound to said capture molecules. The step of measuring step may be performed qualitatively or quantitatively. In some embodiments, step of binding is performed by said composition bonding directly to said substrate, e.g. via hydrogen bonding, or ionic bonding. In some embodiments, the sample is a liquid medium such as, for example, blood, serum, or urine. In one embodiment, the composition is combined with said sample in said combining step in the form of a plurality of particles. In yet another embodiment, at least two of said plurality of particles include different capture molecules (for example, antigens and/or antibodies). Alternatively, the analyte molecules may be antigens or antibodies, and may also be cancer markers. In some embodiments, the measuring step of the method performed in an assay such as ELISA, MALDI or SELDI. In a preferred embodiment, the lyotropic liquid or liquid crystalline material is cubic phase. The method may further comprise the step of coating the lyotropic liquid or liquid crystalline material with a coating, after the step of allowing said analyte molecules in said sample to bind with said capture molecules and before the step of binding said composition to said substrate.

The invention further provides a composition used for calibration in an assay, the composition comprising a plurality of particles formed from lyotropic liquid or liquid crystalline material, which bind directly to a surface of a substrate, each of said plurality of particles having at least two different marker molecules present in the particle. In some embodiments, the particles are coated; in other embodiments, the particles are uncoated.

The invention further provides a method for performing a laser desorption ionization assay. The method comprises the steps of: 1) binding a lyotropic liquid or liquid crystalline material to a surface or substrate on which a sample is or will be deposited; 2) coating a layer of said lyotropic liquid or liquid crystalline material and said sample with a chemical which crystallizes in situ to form an energy absorbing matrix; and 3) measuring one or more compounds of interest in said sample after said binding and coating steps using laser desorption ionization. In one embodiment, the step of coating is performed using a chemical selected form the group consisting of cinnamic acid; cyano-4-hydroxy-cinnamic acid; 3,5-dimethoxy-4-hydroxycinnamic acid; hydroxycinnamic acid-3-phenylpropionic acid; caffeic acid; ferulic acid; 2-(4-hydroxyphenylazo)-benzoic acid; 3-hydroxypicolinic acid; nicotinic acid; 2-pyrazinecarboxylic acid; 2,5-dihydroxybenzoic acid; succinic acid; sinapinic acid and its methyl and dimethyl esters and ethers; 2-amino-4-method-5-nitropyridine; 2-amino-5-nitropyridine; and 6-aza-2-thiothymine. In some embodiments, the binding is performed by said lyotropic or liquid crystalline material bonding directly to said substrate, e.g. by hydrogen bonding or ionic bonding. The lyotropic or liquid crystalline material may incorporate therein one or more marker molecules. Alternatively, the lyotropic or liquid crystalline material may incorporate therein one or more capture molecules. In one embodiments, the lyotropic or liquid crystalline material is bound to said substrate in the form of a plurality of particles. In one embodiment, the particles are coated; in another, they are uncoated. In one embodiment of the invention, the lyotropic liquid or liquid crystalline material is combined with said sample prior to said steps of binding, coating and measuring. In a preferred embodiment, the lyotropic liquid or liquid crystalline material is cubic phase. In various embodiments of the invention, the coefficient of variation in the method is lowered by a factor of 5 or more in the presence of said lyotropic liquid or liquid crystalline material; or by a factor of 3 or more in the presence of said lyotropic liquid or liquid crystalline material; or by a factor of 2 or more in the presence of said lyotropic liquid or liquid crystalline material. In some embodiments, the particle coating comprises a chemical from which said energy absorbing matrix is formed. In other embodiments, the particle coating comprises a chemical selected form the group consisting of cinnamic acid; cyano-4-hydroxy-cinnamic acid; 3,5-dimethoxy-4-hydroxycinnamic acid; hydroxycinnamic acid-3-phenylpropionic acid; caffeic acid; ferulic acid; 2-(4-hydroxyphenylazo)-benzoic acid; 3-hydroxypicolinic acid; nicotinic acid; 2-pyrazinecarboxylic acid; 2,5-dihydroxybenzoic acid; succinic acid; sinapinic acid and its methyl and dimethyl esters and ethers; 2-amino-4-method-5-nitropyridine; 2-amino-5-nitropyridine; and 6-aza-2-thiothymine. In one embodiment, the uncoated particles are coated after combining with said sample but before said step of binding.

The invention further provides a method of preventing non-specific binding during an assay that uses a solid support or substrate. The method comprises the steps of: 1) binding one or more capture molecules to a surface of said support or substrate; and 2) binding lyotropic liquid or liquid crystal material to said surface of said support or substrate at locations on said surface where capture molecules are not bound, whereby samples exposed to said support or substrate are presented with one or more regions for enabling specific binding said one or more capture molecules and are blocked from non-specific binding to said surface of said support or substrate by said lyotropic liquid or liquid crystal material. In one embodiment, the step of binding lyotropic liquid or liquid crystal material is performed by depositing said lyotropic liquid or liquid crystal material over said surface of said support or substrate after said step of binding one or more capture molecules to said surface of said support or substrate. In another embodiment, the lyotropic or liquid crystalline material is bound to said support or substrate in the form of a plurality of particles. In some embodiments, the particles are coated; in others, they are uncoated. In some embodiments, the step of binding said lyotropic or liquid crystalline material to said support or substrate is performed by bonding directly to said support or substrate (e.g. by hydrogen bonding or ionic bonding). In a preferred embodiment; the lyotropic liquid or liquid crystalline material is cubic phase.

The invention further provides a particle, comprising: 1) a lyotropic liquid or liquid crystalline matrix; 2) a first coating on a surface of said lyotropic liquid or lyotropic liquid crystalline material; and 3) a second coating on a surface of said first coating, said second coating being different chemically and/or physically from said first coating. The second coating may be positively or negatively charged, and/or may be capable of hydrogen bonding. A capture molecule and/or a molecular marker may be incorporated in the particle. In a preferred embodiment, the lyotropic liquid or liquid crystalline material is cubic phase.

The invention further provides a particle, comprising: 1) a lyotropic liquid or liquid crystalline matrix; and 2) a constituent associated with said lyotropic liquid or liquid crystalline matrix which, upon activation by a change in pH, temperature, or other physical or chemical condition, forms a coating on said lyotropic liquid or liquid crystalline matrix, said coating causing said particle to bind directly to a surface of a substrate. A capture molecule and/or a molecular marker may be incorporated in the particle. In a preferred embodiment, the lyotropic liquid or liquid crystalline material is cubic phase.

DETAILED DESCRIPTION OF THE PREFERRED EMBODIMENTS OF THE INVENTION

Figure 1:
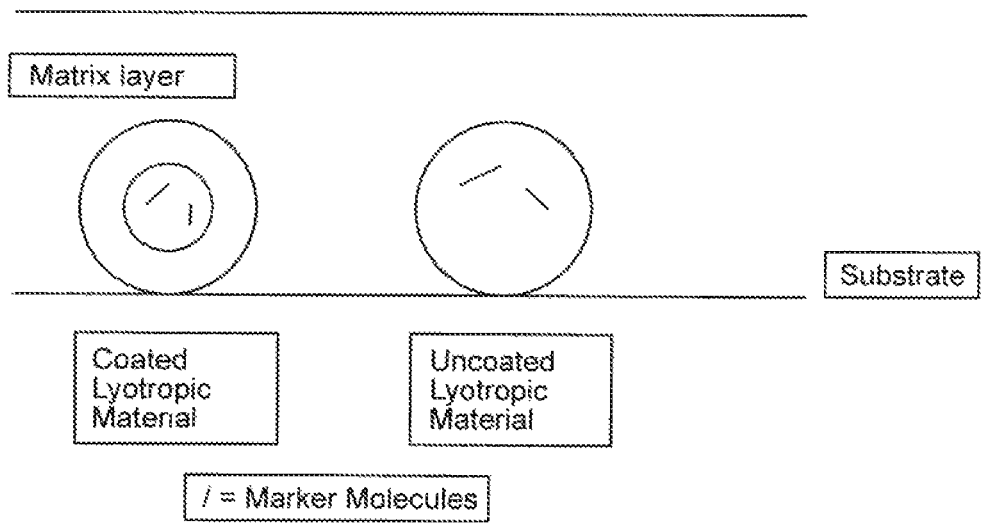
FIG. 1. A schematic representation of a marker molecule in material binding to a substrate used in a MALDI or SELDI type system.
Figure 2A:
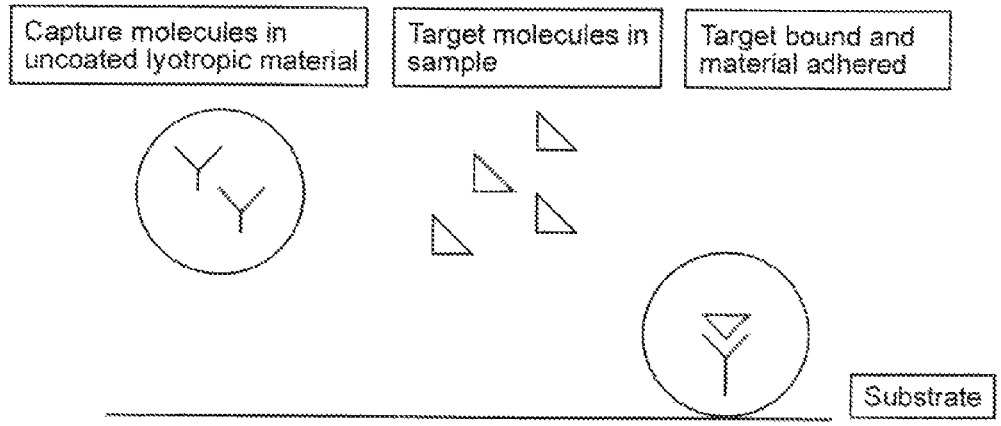
FIGS. 2A and B. A schematic representation of capture molecules with bound analytes in material binding to A, an assay substrate, and B, a SELDI substrate.
Figure 2B:
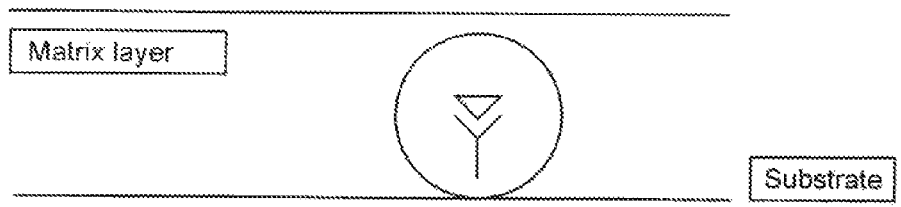

Compositions of lyotropic materials (such as lyotropic liquids or liquid crystalline materials), and methods for their use with respect to binding to assay substrata are herein disclosed. In one embodiment, macromolecules such as captured markers or standards are contained within the lyotropic material, and the compositions stably bind to surfaces such as those used for the substrata of many assay systems. The standards are thus immobilized on the assay surface by virtue of being within the lyotropic material, and are protected from components of biological samples (e.g. proteases), and the accuracy of measurements that rely on the standards is thus enhanced. An exemplary assay surface is the surface of SELDI-MS chips. Exemplary standards include biologically relevant macromolecular species such as proteins, peptides, dendrimers, nucleic acids, polysaccharides, etc.

Nanostructured lyotropic liquid and liquid crystalline phase materials suitable for use in the present invention, have been described, for example, in U.S. Pat. Nos. 6,482,517 and 6,638,621, (both to D M Anderson), the complete contents of which are hereby incorporated by reference. These patents describe coated particles of nanostructured lyotropic liquid and liquid crystalline phase materials with preselected surface chemistries including ionic, hydrophobic, and hydrogen bonding, as well as the presence of antibodies, lectins, nucleic acids, receptors, chimera, avidin, and other biospecific targets at or near the surface of the particles. Both materials and methods of making such particles are discussed in detail in these patents, which also describe the incorporation of macromolecules such as proteins in the nanostructured interior of the particles.

Such coated particles, with macromolecules of appropriate molecular weight(s) incorporated in the interior (and thus sequestered and protected against potentially degrading influences such as proteases or nucleases), can further comprise a coating capable of binding to an assay substrate such as a SELDI substrate. Therefore, such coated particles are especially preferred in certain applications of this invention. In particular, ionically charged coatings such as ionic surfactants or polyelectrolytes can be incorporated in the context of the instant invention, either as described in the methods of U.S. Pat. Nos. 6,482,517 and 6,638,621 for coating nanostructured liquid and liquid crystalline phase materials, or as second (or higher) coatings upon first coatings achieved by those methods. For example, where U.S. Pat. No. 6,638,621 describes a method for producing a liquid crystalline particle coated with a crystalline shell material of zinc-acetyltryptophanate, the present disclosure describes a method for putting a second coating on such a coated particle (containing embedded protein markers), such as to achieve a strong, preselected ionic charge or hydrophobically-interacting surface chemistry.

Thus, in this disclosure new compositions and methods are described in which coated particles are subjected to a second coating process, where the second coating is chosen, for example, for its plate-binding and low-solubility characteristics. In general, it is much simpler to apply a coating to a solid-coated particle than to an uncoated liquid or liquid crystalline particle. This yields particles with two, substantially nested, coatings, wherein the substantially outermost coating binds effectively to the desired assay substrate. The first (inner) coating is selected on the basis of compatibility with the nanostructured liquid or liquid crystalline matrix, and may be formed using the coating methodologies discussed in U.S. Pat. No. 6,638,621, or on the basis of pre-existing or to be discovered technology and practice for making coated liquid or liquid crystalline particles. Once this coating has been applied, application of the second (outer) coating can proceed without limitations imposed by the liquid or semi-solid nature of the matrix, since this is now coated by a solid. Indeed, in the course of this work the application of a second coating was found to be surprisingly robust, particularly in the case where a zinc-N-acetyltryptophan first coating was applied. A range of second coatings was applied under conditions that might have been incompatible with the particles absent the first zinc-NAT coating. Several of these coatings, and the particles so coated, were found to exhibit excellent binding to SELDI plates of various surface chemistries. N-acetyltryptophan is known to have stabilizing effects on proteins (for example, it is used to stabilize albumin, in several commercially available formulations of human albumin for injection), providing another reason why it is a good choice for the first coating since this is in direct contact with the nanostructured liquid crystalline (in this case) matrix containing the embedded protein.

Significantly, it has been discovered that certain compositions are able, in a turn-key fashion, to be used in the following protocol resulting in extremely high and sharp SELDI-MS intensities for a calibration peak:
1) contact the composition (in some cases after dilution), containing a macromolecule associated with a carrier particle, with a biologically relevant material;
2) contact an appropriate substrate for an appropriate length of time with the composition;
3) rinse the substrate.

This straightforward protocol results in a significantly greater deposition of the macromolecule on the substrate than occurs in the absence of the carrier particle. In some embodiments of the invention, the macromolecule is greater than 1,000 in molecular weight, and is most preferably a peptide, protein, or less preferably a polysaccharide or dendrimer. The enhancement factor, namely the ratio of the peak intensity in the carrier particle-macromolecule system to that in the absence of the carrier particle, is preferably greater than about 2, more preferably greater than about 10, and most preferably greater than about 100.

The following definitions and concepts will be useful.

"Assay": in the context of the instant invention, an assay is a qualitative or quantitative measurement or detection of a specific substance of biological or biochemical importance. Furthermore, in the context of this invention the assays of interest are heterogeneous, since they involve a solid-phase substrate.

Examples of assay types for which the instant invention can be useful are: assays based on mass spectrometry techniques, including but not limited to MALDI-MS and SELDI-MS; ELISAs; radioimmunoassays; fluorescence immune assays; electrospray ionization mass spectrometry; chemiluminescent assays; surface plasmon resonance analysis; indirect immunofluorescence assays; nucleic acid hybridization assays; polymerase-chain-reaction-based assays; multiplex assays; and chromatography-based assays. In the latter case, a chromatography bead or bonded phase serves as the substrate to which particles of the instant invention bind, and such an assay can be particularly useful in that it can be preparative, allowing the extraction and/or purification of a captured or encapsulated compound. Overall, the field of "biochips" is an exploding field that will continue to produce new assay techniques and formats, many of which will be amenable to the materials and methods of this invention.

"Substrate": a substrate is a solid surface, not part of a living organism and thus substantially artificial, which has as its main purpose in the context of this invention to provide a controlled and well-characterized surface for deposition of one or materials of importance in a diagnostic assay. While a substrate may contain one or more biological components, its predominant solid or solid-like behavior is established by material that is far removed from living tissue, as, for example, paper is removed from the living tree from which is was derived.

"Marker": in the context of this invention, a marker is a compound whose presence and level in an organism is (or in the case of an autopsy or archeological investigation, can be) correlated with a particular physiological condition, often though not always a disease or injury state, or less commonly with drug usage, nutritional habits, stress, or other physiologic condition.

Peptides, proteins, and other compounds amenable to solid-phase assays as discussed herein, which are of importance in current biomedical practice and research are well known in the art, and U.S. Pat. No. 6,638,621 provides a listing of some of these compounds for which antibodies are currently available. Especially preferred analytes are: TGF-alpha MMP-2, and IGF-II, thyrotropin (TSH), triiodothyronine, thyroxine, free thyroxine, follitropin, lutropin, prolactin, beta subunit of human chorionic gonadotropin, cortisol, ferritin, alpha-fetoprotein, carcinoembryonic antigen, and prostate-specific antigen, somatostatin, angiotensin, insulin, LHRH, CA125, TATI, and neuron-specific enolase (NSE). In addition to these well-characterized markers, MALDI and SELDI analyses of serum from blood pools of cancer-free and cancer patient groups has revealed key markers of certain cancer types that are not yet identified, and appear to be fragments of proteins leftover from pathological lysis of proteins, and these are of particular importance in the context of this invention.

"Lyotropic liquid crystalline phase": lyotropic liquid crystalline phases include the normal hexagonal, normal bicontinuous cubic, normal discrete cubic, lamellar, reversed hexagonal, reversed bicontinuous cubic, and reversed discrete cubic liquid crystalline phases, together with the less well-established normal and reversed intermediate liquid crystalline phases. All of the lyotropic liquid crystalline phases are characterized by domain structures, composed of domains of at least a first type and a second type (and in some cases three or even more types of domains) having the following properties:

a) the chemical moieties in the first type domains are incompatible with those in the second type domains (and in general, each pair of different domain types are mutually incompatible) such that they do not mix under the given conditions but rather remain as separate domains;

b) the atomic ordering within each domain is liquid-like rather than solid-like, lacking lattice-ordering of the atoms; (this would be evidenced by an absence of sharp Bragg peak reflections in wide-angle x-ray diffraction);

c) the smallest dimension (e.g., thickness in the case of layers, diameter in the case of cylinders or spheres) of substantially all domains is in the range of nanometers (viz., from about 1 to about 100 nm); and d) the organization of the domains conforms to a lattice, which may be one-, two-, or three-dimensional, and which has a lattice parameter (or unit cell size) in the nanometer range (viz., from about 5 to about 200 nm); the organization of domains thus conforms to one of the 230 space groups tabulated, for example, in the International Tables of Crystallography, and would be evidenced in a well-designed small-angle x-ray scattering (SAXS) measurement by the presence of sharp Bragg reflections with d-spacings of the lowest order reflections being in the range of 3-200 nm.

"Cubic phase": Such a phase has cubic crystallographic symmetry, which makes it optically isotropic and yields characteristic indexings of the Bragg peaks in SAXS, corresponding usually to one of the space groups Im3m, Pn3m, or Ia3d. The bicontinuous property, in which both polar and apolar components are simultaneously continuous in all three dimensions, gives rise to high self-diffusion coefficients of all components of low MW, whether they are segregated into the polar or the apolar domains, and also gives rise to high viscosities, often in the millions of centipoise. This phase generally appears at lower water contents than lamellar phases, and/or at higher water contents than reversed hexagonal phases, and can also sometimes be induced by adding a hydrophobic component to a lamellar phase, or a non-surfactant amphiphile with a weak polar group. When this is the phase used in the practice of this invention and it is desired to have this in contact with a solvent then the solvent should preferably be a polar one, typically water or aqueous buffer, but more generally a polar solvent or mixture thereof. The pore size can be adjusted by changing the composition, and be determined precisely.

Some of the favorable features that distinguish reversed cubic phases as being especially preferred in the context of this invention are as follows.

Lipid-dense, high internal surface area: with lipid concentrations typically on the order of 30-50%, and every point in the cubic phase lying within a few nanometers of both an aqueous domain and a lipid bilayer, cubic phases are superior matrices for biomacromolecules. It cannot be overstated that in contrast with the common misconception that a given molecule is situated, at any given moment, either in an aqueous or an oily domain, in actual fact most proteins have a strong propensity to situate so as to straddle the polar-apolar interface (the dividing surface between the polar head groups and apolar chains of the lipid). NMR analyses have shown that even long-chain alcohols—highly hydrophobic compounds with but a single polar group at their end—are situated so that the hydroxyl group is strongly bound at the polar-apolar interface. In the case of biomacromolecules, a great deal is known about the registry between polar and apolar epitopes of membrane-associated proteins with those of the lipid bilayer. Specific surface areas in typical cubic phases, measured over the polar-apolar (hydrophilic-hydrophobic) interfacial surfaces, are in the range of 200 $m^2/gm$. As a result, typical loadings of proteins achievable in cubic phases are 30% by weight, and partition coefficients so high that water-phase concentrations are below detection limits. Together these properties of high loadings and high partition coefficients mean that crucial proteins including markers can be imbibed from assay solutions and maintained in solution within the cubic phase. A protein can be said to partition strongly into a liquid crystal when the partition coefficient, measured between the liquid crystal and aqueous buffer (as opposed to the traditional measurement between octanol and water) is greater than about 100, more preferably greater than about 1,000 and most preferably greater than about 10,000.

High bilayer fluidity: the bilayer fluidity (which refers specifically to the microviscosity in the bilayer, and is substantially independent of the viscosity of the macroscopic material) of the cubic phase permits dissolution and both orientational and diffusional freedom of macromolecules within the bilayer, and can be of critical importance in affording the proper presentation of capture molecules. This is of crucial importance in the current invention.

Highly viscosity and pseudoplasticity: the three-dimensional, lattice-ordered supermolecular structure of cubic phases gives rise to extremely high zero-shear viscosities, measured in the billions of centipoise, but modest shear transiently breaks the structure and reduces the viscosity by many orders of magnitude. Cubic phases behave essentially as solid-like materials under low-shear conditions, making for structural permanence that distinguishes them from thermally roiled materials such as micellar solutions and micelles, but that only mild shear conditions are needed to break the materials into microparticles. In the current invention, shear requirements can be further reduced by judicious application of phase diagram information, circumventing the need for high-pressure homogenization as required in, e.g., liposome production. Delicate, shear-sensitive biopharmaceuticals can therefore be encapsulated in robust, protective matrices without exposure to harsh conditions.

Permselective accessible aqueous porosity: the nanoporous-network structure of the cubic phase, such that the 3-dimensional network of aqueous pores lacing the entire particle is accessible from the outside for molecules smaller than the poresize, is a feature that clearly distinguishes reversed cubic phase from liposomes and emulsions, by providing ready accessibility of analytes and assay-associated molecules to compounds in cubic phase particles and films. Due to the uniform poresize in these lattice-ordered materials, where said poresize can be substantially pre-selected and tuned by composition over the size range that covers the range of protein dimensions, it is possible to formulate particles that can allow the passage of peptides but exclude degradative proteins such as proteases. This is of particular potential importance in the case of SELDI-based early cancer detection methodologies, where the markers have been found to be peptides and small fragments of proteins.

Particle stability. Stability is one feature in which particles of the instant invention excel over certain other materials, such as liposomes for example. Uncoated particles of cubic phase, as exemplified by the propofol dispersion described in Example 3 below, exhibit excellent long-term (2+ years) stability when stored at room temperature, and excellent accelerated stability (45° C.) over 9 months or more as well. Particle sizes as measured by light scattering show virtually no change over the lifetimes cited. Particles coated with zinc-NAT, exemplified by a number of Examples below, exhibit long-term stability at room temperature, and furthermore stabilize sensitive actives by virtue of the coating. This stability is accomplished within the realm of high-fluidity bilayer materials, as discussed above.

Particle shape. In contrast with liposomes, particles composed of cubic phase, whether coated or not, appear to have a strong tendency to assume polyhedral forms, which can allow them to more intimately bind to solid substrata over a larger footprint. The polyhedral form is essentially a manifestation of a crystal habit, albeit in this case in the context of a supermolecular liquid crystal, which nevertheless conforms to a cubic crystallographic space group. This feature represents a distinction from, and advantage over, spherical particles such as liposomes, particularly liposomes made from high-transition temperature lipids that yield rigid bilayers, which do not conform well to surfaces in general.

Thus, milieu-sensitive proteins and biomacromolecules can be captured and sequestered within dispersed cubic phase particles, protected by virtue of permselectivity inherent in the accessible cubic phase porosity and/or by one or more coatings, bound by capture molecules that are virtually assured of near-physiologic conformation, and deposited on a substrate through particle-substrate affinity that can be independent of capricious protein-substrate interactions. It should be noted that the ability of a particle to deposit a particular compound onto a substrate independently of the compound-substrate interaction (that is, independently of whether or not it would bind without a particle being present) is at least to some extent dependent on having a very low-solubility coating. In view of the high dilutions that are typically used in ultrasensitive techniques like SELDI, even a small aqueous solubility of the particle coating can result in the stripping away of the coating and contact between the compound and substrate, introducing compound-substrate interactions back into the picture.

"Bilayer-associated", "membrane-associated": A compound or moiety is bilayer-associated if it partitions preferentially into a bilayer over an aqueous compartment. Thus, if a bilayer-rich material such as a reversed cubic phase material exists in equilibrium with excess water and is placed in contact with excess water, and a bilayer-associated compound or moiety is allowed to equilibrate between the two phases, then the overwhelming majority of the compound or moiety will be located in the bilayer-rich phase. The concentration of the compound or moiety in the bilayer-rich phase will be at least about 100 times, and preferably at least about 1,000 times, larger than in the water phase.

It is important to note that although the reversed hexagonal phases and reversed discrete or discontinuous cubic phases do not have a true bilayer as the fundamental structural unit, in the present disclosure we will nevertheless use the term "bilayer-associated" to describe components that partition into the lipid-rich (or surfactant-rich) microdomains irrespective of whether such domains are considered "monolayers" or "bilayers". The term "bilayer-associated" is thus more directed to the partitioning of the compound in question than to the precise nature of the lipid (or surfactant) region.

Besides capture and bilayer-charging compounds, another component of the particle that can be bilayer-associated is the biomolecule or standard itself. For small molecules, this is preferred, since it means that the biomolecule will tend to remain with the particle even when the particle is exposed to large volumes of biological fluids. However, biomolecules that partition preferentially into the aqueous channels of the reversed liquid crystalline material, including many if not most proteins and other biomacromolecules, can be incorporated into particles utilized in the current invention, as can biomolecule that localize to comparable concentrations in the aqueous and hydrophobic compartments. Indeed, one important aspect of the invention which distinguishes it over typical emulsions, for example, is the very large polar-apolar surface areas, which provide ample volume for biomolecules which have apolar groups or epitopes that prefer a hydrophobic milieu as well as polar groups that prefer the hydrophilic milieu of the aqueous channels and head group-rich regions.

"Energy-absorbing matrix": For MALDI-MS, SELDI-MS, and related applications, "energy-absorbing matrices" are those that can serve as the matrix which interacts with laser light to break up the material on the substrate and fly (propel) the material down the flight tube. Examples of such coatings include the following acids: cinnamic acid; cyano-4-hydroxy-cinnamic acid; 3,5-dimethoxy-4-hydroxycinnamic acid; hydroxycinnamic acid-3-phenylpropionic acid; caffeic acid; ferulic acid; 2-(4-hydroxyphenylazo)-benzoic acid; 3-hydroxypicolinic acid; nicotinic acid; 2-pyrazinecarboxylic acid; 2,5-dihydroxybenzoic acid; succinic acid; and sinapinic acid and its methyl and dimethyl esters and ethers. Bases are also used, such as 2-amino-4-methyl-5-nitropyridine and 2-amino-5-nitropyridine; 6-aza-2-thiothymine.

Methods and Materials.

An important aspect of the instant invention is the crafting of lyotropic liquid or, more preferably, liquid crystalline material, so as to bind to a substrate either as a collection of particles or as a film, which in turn may or may not be coated. In some cases, the lyotropic material and the substrate will be chosen together, in tandem, so as to yield the desired binding. This can be accomplished by judicious use of one or more of the following three general approaches:

A) coating: particles are at least partially covered with a coating material that is selected so as to bind to the substrate;

B) compound in the lyotropic material: the lyotropic material is chosen so as to incorporate one or more compounds that promote binding of the material to the substrate; most preferably these compounds are bilayer-associated; less preferably, a non-bilayer-associated compound in the lyotropic material is retained in the material by a gelation step that is carried out within the lyotropic material;

C) hydrophobic interaction: the lyotropic material and substrate are selected in such a way that a hydrophobic interaction between the two promotes binding.

Detailed descriptions of methods for producing particles of lyotropic materials coated with a wide range of coating materials are given in U.S. Pat. No. 6,482,517 and U.S. Pat. No. 6,638,621, the contents of which are incorporated herein by way of reference, and the discussion below describes how such methods can be incorporated into embodiments of the instant invention. Similarly, concerning the second approach, detailed descriptions of methods for producing uncoated particles of lyotropic materials containing bilayer-associated compounds, as well as capture compounds such as antibodies and lectins, are given in U.S. application Ser. Nos. 10/889,313 and 10/170,214. Whereas the latter reference teaches the use of particles incorporating capture (or "target", in the terminology used in that disclosure) molecules in particle interiors for the purpose of capturing molecules in solution for liquid-phase assays, the instant invention by contrast teaches, among other things, the incorporation of capture molecules at particle surfaces in order to obtain binding of particles to properly selected solid substrata for solid-phase assays. Concerning methods of gelation inside lyotropic materials, U.S. Pat. No. 5,244,799 and, particularly, U.S. Pat. No. 5,238,613, the contents of which are hereby incorporated by reference, describe methods and materials for accomplishing this, and this is discussed in the context of the instant invention below.

This approach first involves the selection of a pair of materials, one to serve as the substrate and the other as a coating on a coated lyotropic liquid or liquid crystalline material, or as a particle-bound compound at the surface of (and possibly inside of, as well) an uncoated particle, or as the lipid or surfactant in an uncoated particle designed for hydrophobic interaction-based binding. In many cases, the choice of substrate will be in part, or fully, driven by considerations that have nothing to do with the lyotropic material. For example, one may be dealing with a substrate that is chosen so as to bind certain compounds independently of (and perhaps along with) any lyotropic particles or materials, or to be compatible with certain experimental conditions such as high local radiation intensities, low nonspecific binding characteristics, or the like. In any case, with a given substrate in mind, the invention contemplates the judicious choice and application of particle composition, in particular of the particle surface, so as to achieve the desired particle deposition and binding.

The substrate-particle binding in the instant invention will be achieved by virtue of one or more favorable interactions selected from the group that includes the following: electrostatic (anion/cation pairing), hydrophobic interaction, hydrogen bonding, polymer bridging, surface dehydration, van der Waals attraction involving a high-energy surface, magnetic, antibody/antigen, lectin/saccharide, nucleic acid/complementary nucleic acid, receptor/ligand, and other protein binding interactions such as avidin/biotin, etc. (Here the forward slash terminology A/B means A binding to B). The preferred binding mechanisms, both in the case of coated and uncoated particles, for typical applications, will be those involving strong, non-biospecific attractive forces such as electrostatic and hydrophobic interaction forces, because biospecific mechanisms such as receptor/ligand interactions typically involve more delicate proteins that can denature, e.g., when adsorbed to a solid-coated particle, absent more sophisticated tethering schemes. However, in more critical applications, particularly those that justify expensive and/or elaborate chemistries (e.g., protein PEGylation or chimeras), biospecific mechanisms can become the preferred means, with antibody/antigen interactions being most preferred.

Generally, in the case where coated particles are used in the current invention with the intention that they bind to the substrate as coated particles (that is, where the coating is the binding entity), the coating material should have a solubility in water of less than about 5%, more preferably less than about 1%, and most preferably less than, about 0.1%, so that the coating does not substantially dissolve when the particles are applied in the assay, which will nearly always be aqueous-based. In case the solubility is not sufficiently low to avoid unwanted dissolution, then the water used in the assay system must be saturated in the coating compound, though this is far less preferred due to deleterious salting-out and dissolution-recrystallization effects. Contrariwise, if the intent is that the particles be formulated and stored as coated particles (e.g., for purposes of stabilization via the coating) but that the coating should dissolve so as to leave uncoated particles for the application, then the reverse is true, and the coating solubility should be greater than about 0.01%, and more preferably greater than about 0.1%. In the case of uncoated particles, the crucial components of the lipid (or surfactant) bilayer should have a water solubility less than about 5%, more preferably less than about 1%, and most preferably less than about 0.1%.

Various particle types and means of binding are now discussed.

Electrostatic Binding.

In SELDI applications, as well as in a wide range of other analytical techniques, it is very common to utilize substrata whose most characteristic feature is a significant surface charge. Indeed, at the current stage of SELDI at the time of this writing, this is by far the most prevalent case. Typically the preferred substrate surface charge is cationic (otherwise known as anion-exchange), since most biological components are negatively-charged at pH values near physiological. Anionic (i.e., cation-exchange) substrata are selective towards the far less common cationic compounds.

In this approach, the surface of the lyotropic particle will be engineered so as to be oppositely charged as the substrate, and zeta potential measurements can be used to determine the charge experimentally. To avoid undue experimentation, this disclosure describes methods and materials for engineering such a particle.

Compounds containing the following chemical groups can be charged, albeit weakly and/or over a fairly narrow pH range: silanol, aldehyde, ketone, carboxylic ester, carboxylic acid, isocyanate, amide, acyl cyanoguanidine, acyl guanylurea, acyl biuret, dimethylamide, nitrosoalkane, nitroalkane, nitrate ester, nitrite ester, nitrone, nitrosamine, pyridine N-oxide, nitrile, isonitrile, amine borane, amine haloborane, sulfone, phosphine sulfide, arsine sulfide, sulfonamide, sulfonamide methylimine, alcohol (monofunctional), ester (monofunctional), secondary amine, tertiary amine, mercaptan, thioether, primary phosphine, secondary phosphine, and tertiary phosphine. Weakly charged coatings are preferred in the present invention in the following contexts: to achieve electrostatic binding while minimizing electrostatic repulsions, and/or unwanted electrostatic attractions, between particles and analytes; as first coatings in doubly-coated particle systems; and for binding the combines electrostatic with hydrophobic-interaction attractions.

Compounds containing the following chemical groups can be strongly charged over some pH range (typically large), are:
  a. Anionic groups: carboxylate (soap), sulfate, sulfonate, sulfonate, thiosulfate, sulfinate, phosphate, phosphonate, phosphinate, nitroamide, tris(alkylsulfonyl)methide, xanthate;
  b. Cationic groups: ammonium, pyridinium, phosphonium, sulfonium, and sulfoxonium.

The use of coatings that incorporate these chemical groups can provide electrostatic stabilization of the particles in dispersed form as during storage and in capture processes prior to substrate binding, as well as electrostatic binding to the substrate of opposite charge. Zeta potential measurements (e.g., employing laser Doppler electrokinetic measurements) are important for validating and quantifying the charge on such particles, and preferably conditions in the exterior aqueous phase are chosen in such an experiment to match reasonably closely the conditions that will be present in the actual binding event, in the application.

Doubly-Coated Particles.

As discussed above, an especially effective method for producing particles of this invention is to use an approach in which coated particles are subjected to a second coating process, where the second coating is chosen for its plate-binding and low-solubility characteristics; as discussed above, it is much simpler to apply a coating to a solid-coated particle than to an uncoated liquid or liquid crystalline particle. This second coating can be applied to coated particles using a wide range of means, including chemical precipitation, spray-drying (e.g., spray-drying a dispersion of coated particles with second coating dissolved or dispersed therein), spray-congealing, fluidized bed coating, electrospinning, sputter-coating, ion-bombardment, etc. Generally, nearly all of the methods discussed in U.S. Pat. No. 6,638,621 for putting a first coating on a lyotropic material after it has been dispersed, can be also applied to coated particles for putting on a second coating. Chemical precipitation is the most preferred, with precipitation accomplished conveniently by a simple acid-based reaction or counterion exchange. In many cases, the second coating can even be the same charge (cationic, anionic) as the first coating, and this is preferred if bridging and flocculation is experienced when an oppositely-charged second coating is used. In the case where a charged second coating is desired, most preferably the first coating is weakly- or un-charged (as is the case with the weakly-charged zinc-NAT first coating used in many of the Examples below).

Especially preferred second coating materials are polymers, lipids, and surfactants of low solubility, including divalent-ion salts and protonated forms of anionic surfactants. Suitable lipids include phospholipids (such as phosphatidylcholine, phosphatidylserine, phosphatidylethanolamine, or sphingomyelin), or glycolipids (such as MGDG, diacylglucopyranosyl glycerols, and Lipid A.) Other suitable lipids are phospholipids (including phosphatidylcholines, phosphatidylinositols, phosphatidylglycerols, phosphatidic acids, phosphatidylserines, phosphatidylethanolamines, etc.), sphingolipids (including sphingomyelins), glycolipids (such as galactolipids such as MGDG and DGDG, diacylglucopyranosyl glycerols, and Lipid A), cholic acids and related acids such as deoxycholic acid, glycocholic acid, taurocholic acid, etc., and low-solubility salts thereof, gentiobiosyls, isoprenoids, ceramides, plasmologens, cerebrosides (including sulphatides), gangliosides, cyclopentatriol lipids, dimethylaminopropane lipids, preferably double-chained or with saturated long chains (14 or more carbons, preferably 16 or more). Preferred surfactants for second coatings are:

anionic—divalent salts and acid forms of alkyl sulfates, dialkyl sulfosuccinates, alkyl lactylates, and carboxylate soaps of the form $IC_n$ where either: a) the chain is saturated and the length n is between 14 and 20 and I is a monovalent counterion such as lithium, sodium, potassium, rubidium, etc.; or b) the chain is unsaturated or branched, or of length n less than about 14, and I is a multivalent counterion;

cationic—dimethylammonium and trimethylammonium surfactants with chloride, bromide or sulfate counterion, myristyl-gamma-picolinium chloride and relatives, where single-tailed quaternary ammonium surfactants have saturated chains with lengths between about 14 and 20 carbons, and double-tailed quaternary ammonium surfactants have saturated chains with lengths between about 10 and 20 carbons;

Polymers preferred for the second coating are: polypropylene oxide, polybutadiene, polyisoprene, polyacrylic acid and its salts, polymethacrylic acid and its salts, polymethylmethacrylate polyacrylamide, polyisopropylacrylamide, polyacrylonitrile, polyvinyl acetate, polyvinyl caprylate, polystyrene, polystyrene sulfonic acid and its salts, pectin, chitin, chitosan, cellulose derivatives, alginic acid and its salts, gum arabic and its salts, gelatin, PVP, tragacanth, agar, agarose, guar gum, carboxymethylcellulose, arabinogalactan, Carbopol, chitin, chitosan, Eudragits, glycogen, heparin, pectin, and complex carbohydrates which can, e.g., bind with specificity to various saccharide-recognizing compounds such as lectins. Chitosan and certain amino-containing Eudragits are of particular importance because they are among the relatively small list of conveniently-available polymers which are cationic, making them useful for binding to anionic substrata.

Uncoated Charged Particles.

For the purpose of binding uncoated particles to cationic (ion-exchange) substrata, a very effective approach is to incorporate into the lyotropic liquid or liquid crystalline material a bilayer-associated anionic compound (and associated counterion), which is sufficient to establish a significantly negative zeta potential on the particles. In view of the high dilutions that are frequently employed in assays, the partition coefficient of this compound in the particle over water needs to be very high, greater than about 100, more preferably greater than about 1,000 and most preferably greater than about 10,000. Fortunately this is the case for a wide range of charged compounds, both anionic and cationic, due to the high interfacial area property of these materials, especially cubic phases, as discussed above.

Especially preferred anionic moieties are: docusate, dodecylsulfate, deoxycholic acid (and related chocolates, such as glycocholate), tocopherol succinate, stearic acid and other 18-carbon fatty acids including oleic, linoleic, and linolenic acids, gentisic acid, hydrophobic amino acids including tryptophan, tyrosine, leucine, isoleucine, aspartic acid, cystine, and their N-methylated derivatives, particularly N-acetyl-tryptophan, myristyl gamma-picolinium chloride, phosphatidylserine, phosphatidylinositol, phosphatidylglycerol (particularly dimyristoyl phosphatidylglycerol), and other anionic and acidic phospholipids. The person with skill in the art will recognize docusate as the anionic moiety of the surfactant docusate sodium (also known as Aerosol OT), and dodecylsulfate as the anionic moiety of the surfactant sodium dodecylsulfate, or SDS. Surface-active polypeptides and proteins, such as casein and albumin, may also be used, although careful attention must be paid to the pH, which will have an effect on the charge of the molecule.

Other compounds that can provide the anion include ascorbyl palmitate, stearoyl lactylate, glycyrrhizin, monoglyceride citrate, stearyl citrate, sodium stearyl fumarate, JBR-99 rhamnolipid (and other biosurfactants from Jeneil Biosurfactant), glycocholic acid, taurocholic acid, and taurochenodeoxycholic acid.

Other preferred anionic surfactants are: sodium oleate, sodium dodecyl sulfate, sodium diethylhexyl sulfosuccinate, sodium dimethylhexyl sulfosuccinate, sodium di-2-ethylacetate, sodium 2-ethylhexyl sulfate, sodium undecane-3-sulfate, sodium ethylphenylundecanoate, carboxylate soaps of the form $IC_n$, where the chain length n is between 8 and 20 and I is a monovalent counterion such as sodium, potassium, ammonium, etc.

Cationic Bilayer-Associated Compounds.

For binding to anionic substrata, cationic bilayer-associated compounds for incorporation into uncoated lyotropic particles include: myristyl-gamma-picolinium chloride, benzalkonium chloride, tocopheryl dimethylaminoacetate hydrochloride, Cytofectin gs, 1,2-dioleoyl-sn-glycero-3-trimethylammonium-propane, cholesterol linked to lysinamide or ornithinamide, dimethyldioctadecyl ammonium bromide, 1,2-dioleoyl-sn-3-ethylphosphocholine and other double-chained lipids with a cationic charge carried by a phosphorus or arsenic atom, trimethyl aminoethane carbamoyl cholesterol iodide, O,O'-ditetradecanoyl-N-(alpha-trimethyl ammonioacetyl) diethanolamine chloride (DC-6-14), N-[(1-(2,3-dioleyloxy)propyl)]-N—N—N-trimethylammonium chloride, N-methyl-4-(dioleyl)methylpyridinium chloride ("saint-2"), lipidic glycosides with amino alkyl pendent groups, 1,2-dimyristyloxypropyl-3-dimethylhydroxyethyl ammonium bromide, bis[2-(11-phenoxyundecanoate)ethyl]-dimethylammonium bromide, N-hexadecyl-N-10-[O-(4-acetoxy)-phenylundecanoate]ethyl-dimethylammonium bromide, 3-beta-[N—(N',N'-dimethylaminoethane)-carbamoyl, and particularly useful is didodecyldimethylammonium bromide.

Other Useful Bilayer-Associated Compounds.

Other suitable charged bilayer-associated compounds for use in uncoated particles of the instant invention, which can take up a charge under at least some conditions, include: fatty acids, phenolic compounds such as eugenol, isoeugenol, quinolines, hydroxyquinolines and benzoquinolines, tricyclics such as carbazole, phenothiazine, etc., pigments, chlorophyll, certain natural oil extracts particularly those which are phenolic (such as clove oil, ginger oil, basil oil), biosurfactants (such as Jeneil's "JBR-99"), a wide range of dyes. Amphiphilic proteins and polypeptides can be used, including gramicidin, casein, albumin, glycoproteins, lipid-anchored proteins, receptor proteins and other membrane proteins such as proteinase A, amyloglucosidase, enkephalinase, dipeptidyl peptidase IV, gamma-glutamyl transferase, galactosidase, neuraminidase, alpha-mannosidase, cholinesterase, arylamidase, surfactin, ferrochelatase, spiralin, penicillin-binding proteins, microsomal glycotransferases, kinases, bacterial outer membrane proteins, and histocompatibility antigens. As is well known, every protein has a net charge except at its isoelectric point (pI), and thus a membrane-associated protein is suitable for use in the present invention as long as the pH is away from its isoelectric point. A few such proteins are currently accepted as inactive ingredients for pharmaceutical preparations, at least under some conditions, and these include gluten, casein, and albumin.

Charged Gels.

As introduced above, another method for establishing a retained ionic charge on an uncoated lyotropic particle, which need not involve bilayer-associated compounds, is to perform a gelation of a charged compound (monomer, oligomer, prepolymer, gelling polymer) inside the pores of a lyotropic material. Nature provides a number of charged polymers (typically polysaccharides) which can be gelled under mild conditions. These include gelatin, guar gum, pectin, alginic acid and its salts, gum arabic and its salts, tragacanth, agar, agarose, glycogen, heparin and the semisynthetic compounds carboxymethylcellulose, Carbopol, chitosan, Eudragits, as well as a number of proteins which can be made to gel, such as casein, gluten, and albumin (note that the latter tend to be membrane-interactive by virtue of amphiphilicity). The gelation can be carried out in the bulk lyotropic material, and the resulting gelled material then dispersed. Alternatively, if the dispersing can be performed before the gelation step without leading to gelation outside the particles, then that is preferred.

Hydrophobic Interaction-Based Binding.

Hydrophobic interaction is an excellent choice in general for the use of the instant invention in SELDI and other assays, since the particles of the invention are inherently well suited for this mechanism of binding. Since lyotropic liquids and especially liquid crystals are rich in surfactant, and in fact depend on hydrophobic interactions between the components for their structure, they bind well to hydrophobic interaction substrata. Furthermore, coating materials are, virtually by definition in these embodiments, of low-solubility in water, in order to perform their job as coatings. Thus, whether coated or uncoated, the lyotropic materials discussed in this disclosure are quite broadly well-suited for HI-based binding to a substrate. This is demonstrated in Example 2 below where the "H50-8" SELDI chips showed a modest but significant amount of binding with two of the embodiments of this invention. Doubly-coated particles in which the second (outermost) coating is hydrophobic can be especially effective at binding, and can be stabilized in aqueous dispersion by the adsorption of very small amounts of surfactant, retaining the HI-based binding of the particles.

Biospecific Binding.

The methods discussed herein, as well as those in U.S. Pat. No. 6,638,621 describing coated particles incorporating proteins and other biomolecules, and U.S. application Ser. No. 10/889,313 describing uncoated particles likewise incorporating biomolecules, can be used as part of a methodology in which one member of an A/B biospecific binding pair (e.g., A=antibody, B=corresponding antigen) is incorporated into the particles, and the other immobilized on the substrate. "Biochips" incorporating attached biomolecules of importance in assays are becoming increasingly used in a number of fields, so that a range of biomolecule substrata are becoming available. Selecting such a substrate and a paired compound for biospecific binding to the biomolecule bound on that substrate, one is then faced with the job of producing a lyotropic particle, coated or uncoated, incorporating that paired compound. The methods of U.S. Pat. No. 6,638,621 and Ser. No. 10/889,313 can be applied to solve that problem, and in the context of the present invention this is simplified relative to the cases of focus in those disclosures, because there is little if any need to limit oneself to formulations containing only low-toxicity compounds, as was required in the pharmaceutical applications of most focus in those disclosures.

Other Compound Pairs.

In addition to the above means of establishing binding, the invention can take advantage of certain specific compound pairs that bind together, in spite of the fact that they may not neatly fit into one of the paradigms discussed above. For example, vitamin B12 (cyanocobalamin) is known to bind tightly to talc and other silicates. Another useful approach is to use a coating that is the same material as, or similar to, the substrate material, and to adsorb, to the surface of the coating, a compound that binds both to the coating and to the substrate. For example, vitamin B12 binds to silicates. Therefore, if the substrate is a silicate, then a silicate-coated particle could be created, to which B12 would be adsorbed, and the particle would be expected to bind to a silicate substrate, with the B12 acting as a sort of "glue" between the two silicate surfaces.

Magnetism-Based Binding.

There are several potential means of producing particles with metallic components that could be directed with magnetic fields to collect at substrate surfaces:

1) Metal coatings on lyotropic materials can be produced by electrodeposition methods, or with the use of reducing agents.
2) Electroplating can deposit metal not only at the surface of, but even in the interior pores of, porous lyotropic materials.
3) Metal particles, particularly nanoparticles, can be embedded into lyotropic materials and particles by vigorous mixing.
4) Metal nanoparticles could be adsorbed onto the surface of lyotropic particles, in analogy with Pickering emulsions.

Binding to Gold Substrata.

Gold is a particularly important substrate surface material. Its inertness, well-characterized nature, high surface energy, and ability to bind albumin are important motivations for using this substrate. When citrate ions are present, albumin can bind to gold surfaces via electrostatic interaction, but albumin binding to gold can occur even in the absence of citrate. Citrate-coated gold is also used as a substrate in some applications. Gold surfaces are often anionic, and the methods and materials described herein for binding electrostatically to anionic surfaces then apply. Thiol compounds can also be attached to gold surfaces, including thioesters and thiocarbonates. In the present invention, promotion of particle binding to gold surfaces can be accomplished by the incorporation of thiol-containing compounds, under conditions that promote attachment of thiol compounds to gold, which are well known; the thiol-containing compound can be incorporated into lyotropic particles in one of three basic ways:

1) by incorporating into the lyotropic material a bilayer-associated thiol compound, which exhibits a high degree of partitioning into the lyotropic material; a thiol-containing lipid, or hydrophobic or amphiphilic protein (with one or more cysteine residues), can provide the required group, preferably on an uncoated particle.

2) by incorporating a thiol-containing compound in the solid or polymeric shell of a coated (or doubly-coated) particle; or 3) by incorporating a thiol group on a tether that is attached, adsorbed, or partially imbibed within, a particle of this invention.

Particles Coatable In Situ.

Particles that can be converted to coated particles by a chemical reaction, for example upon change in, pH and/or addition of a divalent ion such as $Zn^{2+}$, can be of particular advantage in this invention. For example, a particle of cubic phase containing embedded capture molecules, such as antibodies or receptors, can allow access to a particular compound (e.g., antigen or ligand, resp.) before the chemical change which induces the coating, and then after the chemical change and conversion to a coated particle, the advantages of coated particles are gained: permanence, protection of contents, desired binding characteristics, etc. This is demonstrated in Example 12 below, where uncoated particles imbibe fluorescently-labelled albumin and are then coated by simply adding a zinc salt. Coated particles, and ways of making them, are reported in U.S. Pat. No. 6,638,621, and these can yield uncoated-coated convertible particles in the following way. A composition and method of making a coated particle are chosen from the materials and methods given in U.S. Pat. No. 6,638,621, with one criterion being that the method involves first creating a dispersion of uncoated particles, and then forming the coating on the dispersed particles. This coat-forming step inevitably involves some change in condition, such as pH, temperature, pressure, salinity, divalent ion, addition of a reactant, removal of a solvent, etc. This coat-forming condition change is then invoked subsequent to the imbibition or other capture of the desired compounds by the uncoated particles, inducing the coating of the particle preferably with captured compound inside. In some applications it will be important to choose a coat-forming trigger that will not cause denaturation or other diminishment of the molecule(s) of interest. As an example, in the case of the zinc-NAT coatings described in Example 1, the formation of the coating involves three conditions, any one of which can be used as the trigger: addition of NAT, addition of a zinc salt (such as zinc acetate), and addition of base. In this instance, the latter two are preferred because the addition of NAT (as a soluble salt, e.g., with diethanolamine or NaOH) to the cubic phase in water not only aids in the dispersing of the cubic phase into particles, but also preferentially pre-localizes the NAT at or near the surface of the particles which then results in efficient coating upon conversion to zinc-NAT.

Albumin-Bound Markers.

In recent years, SELDI- and MALDI-based research on markers of cancer and other diseases have shown that peptides and proteins of importance as markers often bind to albumin in the blood. This appears to be such a predominant phenomenon that the choice of substrate is often driven largely by the requirement that it bind albumin optimally. In view of this, particles of the instant invention, most preferably uncoated cubic phase particles, which are able to adsorb or, more preferably, to imbibe albumin are potentially of particular importance. Example 12 below provides one case where albumin is readily imbibed into uncoated cubic phase particles, and furthermore that Example teaches how such particles can be subsequently coated by the simple addition of a salt, thus encapsulating the albumin. One skilled in the art will recognize that the conditions used in Example 12 are mild enough that one would expect many, if not most, of the albumin-bound material in the current context to also be encapsulated, in such a process. Discussed herein is also the fact that certain substrata do bind the coated particles created in Example 12.

Another approach possible in the context of this invention is to incorporate into the particles one or more compounds capable of binding albumin, and capturing albumin-associated peptides and materials as well. For example, a mouse anti-human antibody to albumin could be incorporated into, preferably, an uncoated particle.

Interactions of Lyotropic Particles with Energy-Absorbing Matrices.

As seen herein, the instant invention can greatly improve reproducibility and uniformity in MALDI and SELDI applications, accomplishing a reduction in the coefficient of variation (CV) by factor of 2, more preferably by a factor 3 or more, and most preferably by a factor of about 5 or more. The improvement—in some cases dramatic, as seen in Example 8 below)—in reproducibility (and peak intensities as well) due to the application of the current invention may be due to one or more of the following benefits that the invention can provide:

A) In a traditional SELDI assay, the adsorption of proteins to the plate is a dynamic, first-come-first-serve competitive process, which would be expected to yield diminished reproducibility, high CV, whereas in contrast, the imbibition of proteins into a lyotropic particle very quickly reaches equilibrium, due to the fact that the diffusion distance to (and into the interior of) the nearest particle is one micron, rather than several hundred microns as with the normal SELDI assay, by first principles, an equilibrium (or near-equilibrium) process will generally lead to higher reproducibility, lower CV. A several-fold reduction in CV can also be accomplished even if the analyte molecules are adsorbing to the particle surface rather than imbibing into the interior, although the more dramatic improvements would be expected in the latter cases.

Figure 3:
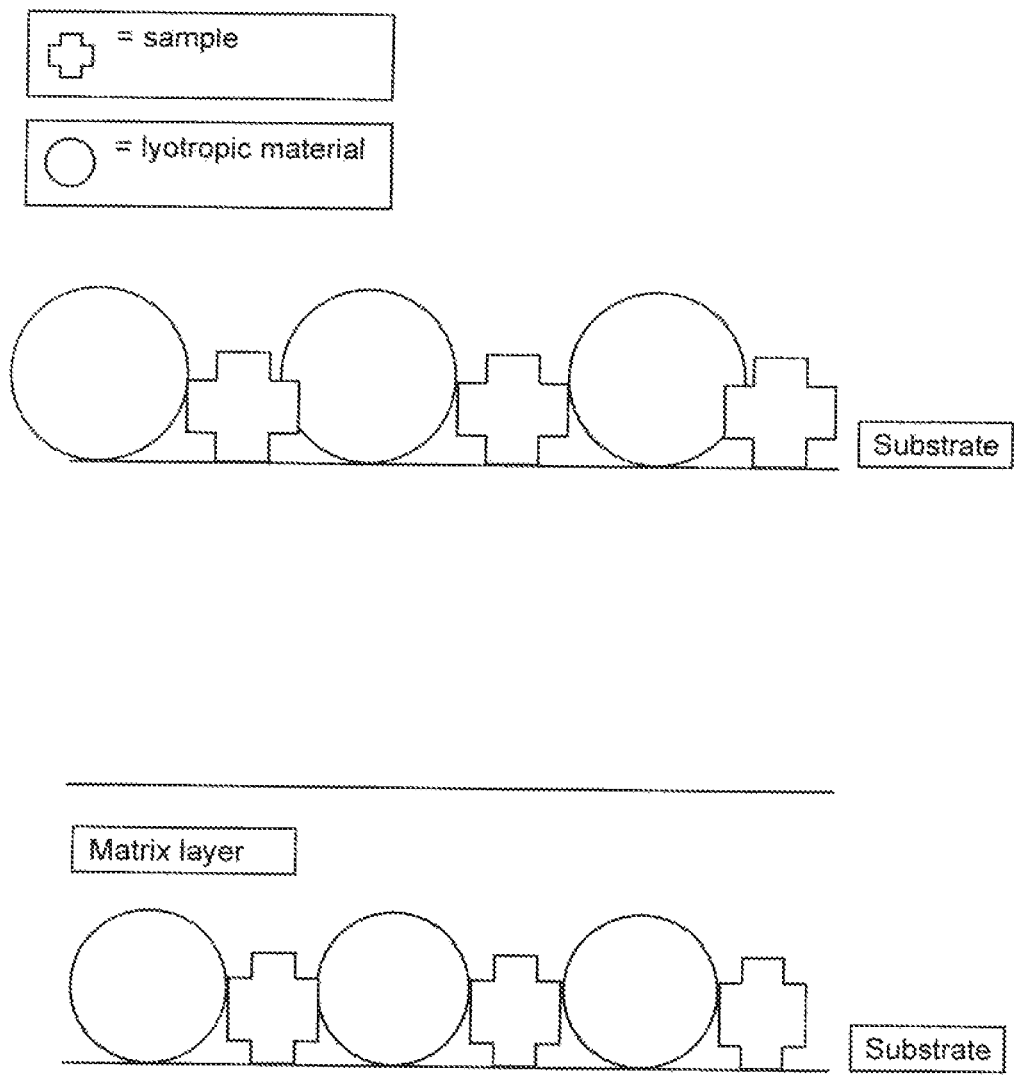
FIG. 3. A schematic representation of material and sample together with matrix material on a substrate used in a MALDI or SELDI type system.
Figure 4:
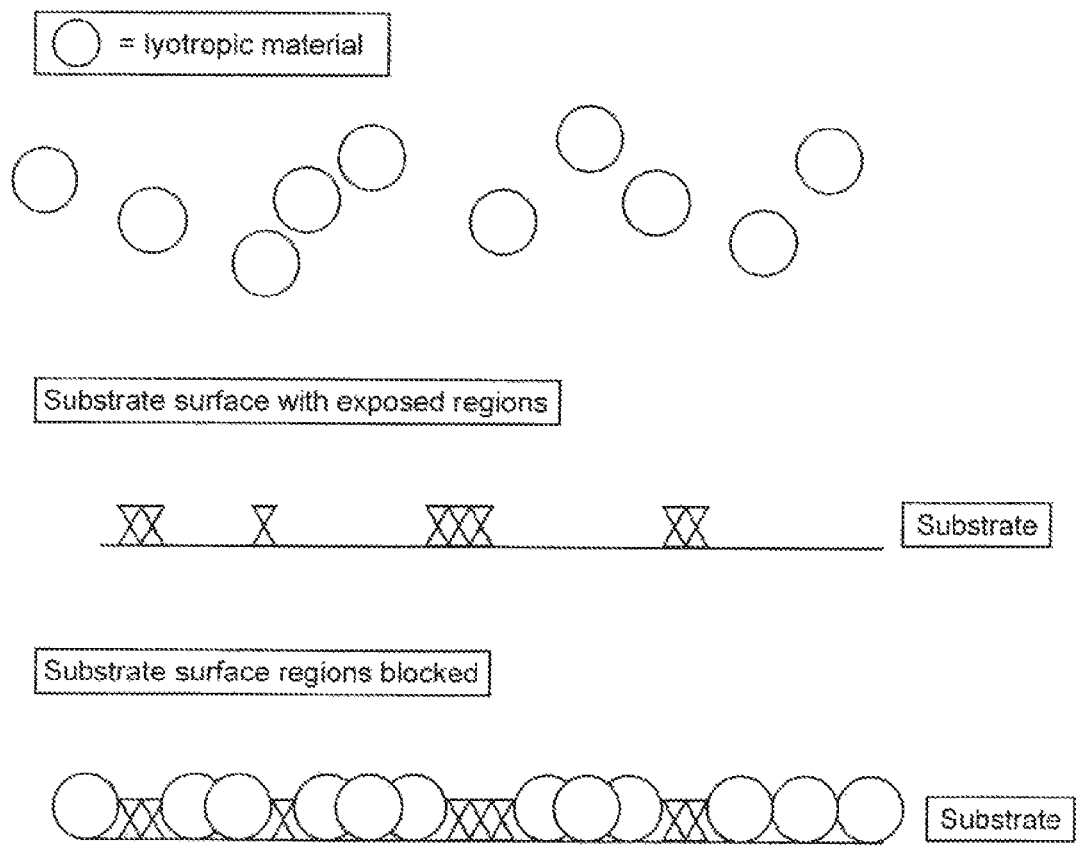
FIG. 4. A schematic representation of material used as a blocking agent on an assay substrate.

B) The presence of lyotropic liquid crystalline particles, preferably those of very high low-shear viscosities, could be improving the nucleation and growth characteristics, and ultimate crystal size and uniformity of deposition, of the energy-absorbing matrix material. Evidence for this is the fact that the crystallization of zinc-NAT (as well as other coatings) is obviously profoundly affect by the presence of dispersed cubic phase particles in our production process for zinc-NAT coated particles—specifically, the crystals take the form of an ultrafine coating on the particles, rather than large, supermicron crystals as is seen in a simple crystallization of zinc-NAT. Indeed, Example 13 below reports how one energy-absorbing matrix material is similarly crystallized in the form of an ultrafine particle coating. If the nucleation, growth, diffusion, or adsorption characteristics of energy-absorbing matrix material is affected in such ways, and particularly if this results in a more intimate association and thus energy transfer between the energy-absorbing matrix and the analyte molecules (which may in turn have imbibed into the particles), then any of these effects could improve peak intensities and reproducibilities. FIG. 3 is intended to depict, schematically, the situation in which the energy-absorbing matrix is intermingled with lyotropic materials of this invention.

C) Since several of the Examples demonstrate that the current invention strongly inhibits non-specific binding, the deposition of proteins and peptides onto the substrate prior to coating is expected to be more predictable and reproducible in the presence of the particles of this invention.

D) The same inhibition of NSB can give rise to more efficient desorption from the substrate (the "D" in MALDI and SELDI).

Lyotropic Particles Coated with Energy-Absorbing Matrices.

Another important type of embodiment of the instant invention involves the use of coated particles, in which the coating actually comprises an energy-absorbing matrix material. Example 13 in fact demonstrates such a particle. The particles can either be supplied in coated form, or can be coated in situ, atop the substrate, after imbibition of analyte in particular (as demonstrated for the case of zinc-NAT coatings in Example 12). Such materials and methods could offer one or more of the following advantages over the prior art practice of MALDI and SELDI:

A) The need for applying the matrix would be circumvented, simplifying and shortening the procedure.

B) Also circumvented would be the organic solvents (acetonitrile, etc) typically used to deposit energy-absorbing matrices in the prior art, and which can result in loss of information due to, e.g., solvent-mediated breakup of intimate protein/peptide complexes.

C) In the case where analyte is sequestered inside of particles subsequently coated, the intimate association between energy-absorbing matrix and analyte can result in superior energy transfer to the analyte and thus more efficient desorption and detection.

More on Uncoated Particles.

Clearly, uncoated particles are of considerable utility in this invention, particularly uncoated particles with significant electrostatic charge. Particles of reversed liquid crystalline phase material, particularly reversed cubic phase and to a lesser extent reversed hexagonal phase, can be stabilized in dispersion by a zeta potential which is greater in magnitude than about 25 millivolts, or more preferably greater than about 30 mV, and this same charge can, in the instant invention, induce binding of the particle to the appropriately chosen SELDI chip. The electrostatic charge is preferably induced by the incorporation, in the liquid crystalline material, of an ionic bilayer-associated compound. Ionic surfactants, and charged compounds with relatively high octanol-water partition coefficients, are incorporated into the liquid crystalline material in order to establish the charge. For the cases where an ionic additive is needed (that is, where the liquid crystalline phase itself does not have a charged surfactant as its main surfactant component), the weight ratio of the charged, bilayer-associated compound to the liquid crystal should be between about 0.01:1 and 0.15:1, or more preferably between about 0.02:1 and 0.08:1. If the charged compound is not a surfactant, it should preferably be a liquid or at least a low-melting compound, that has a high partition coefficient, preferably greater than about 10, more preferably greater than about 100, and most preferably greater than about 1,000. Uncoated particles are particularly useful when the particles are used to capture specific compounds in the analyte (blood, urine, etc.) through either ionic interaction or biospecifically, by the incorporation of capture molecules in the cubic phase such as antibodies, receptors, complementary nucleic acids, chimeras, lectins, saccharides, etc. Likewise, specific interacting pairs such as antibody-antigen, receptor-ligand, RNA-RNA, avidin-biotin, etc., can be incorporated with one part of the pair in the liquid crystalline particle and the other part immobilized on the SELDI chip.

A particularly useful class of embodiments of this invention includes cases where capture molecules, for example antibodies, are incorporated at the surface, and/or in the interior, of liquid crystalline particles, and the particles are added to analyte solution so as to capture specific molecules of interest. In some cases, at least with the current state of art of mass spec-based detection of cancers, the molecule to be captured will not actually be known, except for its molecular weight; in such a case several capture molecules may be tried to determine empirically which is the best for capturing the most important analyte molecules.

Mass spec work to date has shown that there are apparently a handful of compounds, which seem to be peptide fragments, whose presence or level, taken in concert, in blood plasma are indicators of early-stage cancers. While one goal of SELDI-MS is to use the selectivity of SELDI chips to enhance the mass spec signal:noise ratio of these cancer indicators, it may be unrealistic to think that the same SELDI chip can be selective for each one of these indicators. In the instant invention, the SELDI chip need only bind the particle of the invention, not the individual indicators. The job of binding the indicators can be delegated to the particles of the invention, and indeed a single dispersion can contain any number of different particles each selective for as few as one indicator. Furthermore, the incorporation of the capture molecule (such as receptor molecule, lectin, etc.) will in many cases be far superior in a liquid crystalline particle, due to its lipid-based, biomimetic nature, its accessibility via continuous systems of nanopores, and by the tremendous surface areas available for membrane proteins—which can be hundreds of square meters per gram of cubic phase, in particular. Thus, it is entirely practical for a 10 microliter aqueous dispersion of particles of the instant invention to contain 0.1 to 1 square meter (1,000 to 10,000 sq. cm.) of internal surface area, accessible to a molecule with effective diameter less than that of the aqueous pores; this is in sharp contrast with surfaces areas on the order of 0.1 square centimeters for a simple SELDI chip spot. In addition, diffusion of a molecule into a particle of this invention in such a system will involve diffusional distances on the order of one micron, in contrast with 0.1 to 1 millimeter for diffusion to a substrate.

Incorporating Capture Molecules.

Biomacromolecules, especially antibodies, which are particularly useful as capture molecules in the practice of this invention can be selected from the group of compounds that are listed as compatible with liquid crystalline materials in U.S. Pat. No. 6,638,621. Generally speaking, concentrations of these reagents required for the assays of focus herein are not very demanding, and are also sufficiently low that the incorporation of these compounds at the required levels will typically have a minimal effect on the phase behavior of the lipid-based system. This being the case, a pre-existing composition, such as for a cubic phase with desirable properties, can simply be "pulled off the shelf" and the desired compound incorporated, without any particular danger of changing the phase or its properties significantly. The compound can be incorporated most preferably by simply dissolving it in one of the components of the lyotropic liquid or liquid crystalline material, often though not always the aqueous component, which will usually be loaded with buffer components and/or salts, for stabilizing the compound. In some cases, particularly where membrane proteins are involved, lipid and water together will be required to solubilize the protein, but lipids are inherent in the systems of discussion herein. If a membrane protein comes supplied in a lipid-water (or sometimes glycerol) mixture, typically the lipids can be combined and found to be compatible with those of the desired lyotropic composition (with the proper adjustment, of reducing the amount of added lipid in accounting for that already in the protein preparation). In case of highly shear-sensitive compounds, the lyotropic particles can be first dispersed, and the protein or other compound allowed to diffuse into the particles slowly over time under quiescent conditions.

In the case of capture molecules that do not partition strongly into the lyotropic material, this can be remedied by covalently bonding a hydrophobic anchor to the molecule, such as a palmitoyl or oleoyl chain. Compounds reactive to selected groups on proteins that would facilitate such a reaction are available commercially.

Reconstitutable Systems.

A crucial aspect of the embodiments of this invention is the stability of the compositions of the invention. When stored as particle dispersions, the particles should be either substantially free from creaming and flocculation, or be such that creaming or flocculation are easily reversed by simple shaking, prior to use. Reconstitutable dispersions can be of particular value in the instant invention. Spray-drying, freeze-drying, spray-congealing, electrospraying, supercritical fluid methods, and simple vacuum drying are among the ways of drying dispersions that can be applied in the practice of this invention. The appropriate stabilizers must be incorporated so that these powders form dispersions easily upon shaking by hand.

Dendrimers.

Dendrimers are highly-controlled MW compounds that can be used, instead of peptides and proteins, as macromolecules (or "markers") in the practice of this invention. In one type of embodiment, one or more dendrimers is (are) dissolved or dispersed in particles of the invention, and the particles (and therefore the dendrimer as well, by association) are then bound to the desired assay substrate, such as a SELDI chip. One possible complication with the use of dendrimers is their tendency to flocculate proteins, so it is generally best to not include important proteins in the same particles as contain the dendrimers.

Polymerized Materials.

U.S. Pat. No. 5,244,799 (the contents of which are hereby incorporated by reference in entirety) reports the polymerization of nanostructured cubic and hexagonal phase liquid crystals, with retention of their nanostructure. The retention of structure was demonstrated by small-angle x-ray scattering (SAXS) and transmission electron microscopy (TEM). The possibility of polymerizing the cubic phase of a particle of the instant invention opens up a number of possibilities, particularly as they relate to increasing the stability of the reversed liquid crystalline phase and modulating its interaction with proteins, other macromolecules, and also with components of biological materials for analysis. Furthermore, the retention of a bilayer-bound protein might be increased tremendously by polymerization, particularly if polymerization obviated any tendencies for poresize changes with changing conditions. And the presence of a more permanent, precisely-defined pore structure, with precisely tunable poresize, might make possible improved presentation, and/or sequestration of a protein from degradative or other enzymes by size-exclusion from the pores of the polymerized matrix.

EXAMPLES

The following examples illustrate various embodiments of the present invention but are not to be construed as limiting the invention.

Example 1

A reversed cubic phase containing the protein insulin was prepared by first dissolving 0.111 grams of egg yolk ovomucoids (Belovo SA, Inc, Belgium) in 2.112 gm of a 20 mM sodium acetate, 0.5% sodium chloride, pH 4 buffer solution; the latter prepared by dissolving 0.272 gm of sodium acetate (Spectrum Chemical, Gardena, Calif.) and 0.500 gm of sodium chloride (EM Science, Gibbstown, N.J.) in 100 mL of distilled water and adjusting the pH to 4 with 1M hydrochloric acid (Sigma Chemical Company, St. Louis, Mo.). Next, 0.040 gm insulin from bovine pancreas (Sigma Chemical Company, St. Louis, Mo.) was dissolved in the buffer solution, and 0.004 gm phenol (Fisher Scientific, Fair Lawn, N.J.) added. Finally, 3.251 gm linalool (Aldrich Chemical Company, Milwaukee, Wis.), and 3.282 gm of Pluronic P123 (BASF, Mount Olive, N.J.) were added. After thorough mixing the material was optically isotropic and of high viscosity. Of this, 8.384 gm of cubic phase was combined in a 50 mL beaker with 21.002 gm of a diethanolamine-NAT solution; the latter prepared by mixing 8.047 gm of diethanolamine (Aldrich Chemical Company, Milwaukee, Wis.), 18.382 gm of distilled water, and 11.245 gm of N-acetyl-DL-tryptophan (MP Biomedicals, Aurora, Ohio). The cubic phase/diethanolamine-NAT mixture was dispersed first with a Homogenizer (Brinkmann Polytron PT3000) at 29.5 k rpm for three minutes, then with a Microfluidizer Processor (Microfluidics M110L) at 18 k psi for 1.5 minutes. To the microfluidizer was then added 1.902 gm of diethanolamine and 10.309 gm of a 25% wt/wt zinc, acetate solution. Microfluidizing at 18 k psi was continued for 15 runs of 1.5 minutes each, and then 2 mL of hot (60° C.) 6% wt/wt sorbitan monopalmitate dispersion (Spectrum Chemical, Gardena, Calif.) and 2 mL of 15% wt/wt aqueous albumin solution (Sigma Chemical Company, St. Louis, Mo.) were added. Following four more runs in the microfluidizer the dispersion was divided in half.

Twenty mL of dispersion was centrifuged at 13.6 k rpm for 1.5 hours, the supernatant discarded, and the centrifugate reconstituted with 0.5% Tween 80/0.25% SDS solution in a volume equal to that of the discarded supernatant. This reconstituted sample was again dispersed, first with the homogenizer (15 k rpm for 3 minutes) and then with the microfluidizer (18 k rpm for 6 runs of 1.5 minutes each) and finally filtered thru a 5 micron syringe filter. This sample was saved as "Lyotropic/I2D."

The other half of the dispersion was allowed to sit for approximately 24 hours undisturbed, then microfluidized at 18 k rpm for 4 runs of 1.5 minutes each. Next, 5 mL of dispersion was placed into each of 4 centrifuge tubes containing approximately 0.16 gm of GAC 830 Activated Carbon (Norit, Atlanta, Ga.) and the tubes were agitated at 75 rpm for 15 minutes on a shaker (Lab-line Junior Orbit Shaker). Each tube was then centrifuged (Clay Adams compact physicians centrifuge) for 5 minutes at 4800 rpm. The top phase was filtered thru a 5 micron syringe filter and saved as "Lyotropic/I2."

A 10% solution of the cationic polymer Eudragit E100 was prepared by mixing 0.504 gm of Eudragit E100 (Rohm Pharma Polymers, Germany), 0.500 gm of lactic acid (Johnson Matthey, Ward Hill, Mass.), and 4.013 gm distilled water. A 10% solution of the cationic surfactant Myristyltrimethylammonium Bromide was prepared by dissolving 0.507 gm of Myristyltrimethylammonium Bromide (Aldrich. Chemical Company, Milwaukee, Wis.) in 4.509 gm of hot distilled water. A 10% solution of the cationic surfactant Hexadecyltrimethylammonium Bromide was prepared by dissolving 0.501 gm of Hexadecyltrimethylammonium Bromide (Sigma Chemical Company, St. Louis, Mo.) in 4.498 gm of hot distilled water. A 10% dispersion of the anionic surfactant K-Emplex was prepared by mixing 0.502 gm of K-Emplex (American Ingredients Co., Grandview, Mo.) and 4.505 gm of distilled water. The 10% K-Emplex dispersion was vortexed and heated to 75° C.

In separate 8 mL test tubes, 0.5 mL of 10% Eudragit E100 solution was added to 4.50 gm of "Lyotropic/I2" and "Lyotropic/I2D." Next, 1.0 mL of 10% Myristyltrimethylammonium Bromide solution was added to 4.00 gm of "Lyotropic/I2" and "Lyotropic/I2D." Then 1.0 mL of 10% Hexadecyltrimethylammonium Bromide solution was added to 4.00 gm of "Lyotropic/I2" and "Lyotropic/I2D." Finally, 1.0 mL of hot 10% K. Emplex dispersion was added to 4.00 gm of "Lyotropic/I2" and "Lyotropic/I2D." The mixtures were quickly vortexed and sonicated upon each individual addition to disperse.

The samples were named as follows:
- I2-KE: "I2" coated with K-Emplex (sodium stearoyl lactylate)
- I2-E100: "I2" coated with Eudragit E100
- I2-HEX: "I2" coated with hexadecyltrimethylammonium bromide
- I2-MYR: "I2" coated with myristyltrimethylammonium bromide
- I2D-KE: "I2D" coated with K-Emplex (sodium stearoyl lactylate)
- I2D-E100: "I2D" coated with Eudragit E100
- I2D-HEX: "I2D" coated with hexadecyltrimethylammonium bromide
- I2D-MYR: "I2D" coated with myristyltrimethylammonium bromide Zeta potentials, as measured with a Beckmann-Coulter Doppler Electrophoretic Light Scattering Analyzer, were found to average −6 mV for I2D-KE (viz., negative, as expected from the anionic surfactant), and +18 mV for the I2D-MYR sample.

These samples were then used in the Example 2.

Example 2

Doubly-coated microparticle dispersions loaded with the fluorescent dye Rhodamine B base were prepared using the same procedure as in Example 1, then tested for binding to Ciphergen SELDI chips. In each case an aliquot of the dispersion was placed on one SELDI chip spot, incubated for about 15 minutes, and then washed. Using a Reichert-lung Polyvar fluorescence microscope, the fluorescence intensity was recorded as an indicator of particle binding. Four types of Ciphergen SELDI chips were tested: NP20-8, CM10-8, H50-8, and Q-10. Each dispersion was diluted 1 to 10 with Krebbs Ringer buffer (pH 7.4, 4% albumin). Samples were labelled "KE", "E100", "HEX", and "MYR" as follows, with the first and second coatings indicated:
- KE) Zinc-NAT/K-Emplex (sodium stearoyl lactylate)
- E100) Zinc-NAT/Eudragit E100
- HEX) Zinc-NAT/hexadecyltrimethylammonium bromide
- MYR) Zinc-NAT/myristyltrimethylammonium bromide The results were as follows:
- Q-10 chip: KE and E100 showed very intense fluorescence, much weaker for MYR and HEX; E100>KE>>HEX=MYR.
- NP20-8 chip: nothing was very intense or well covered throughout the spot, but KE had some fluorescence; KE>>E100>MYR>HEX.
- CM10-8 chip: HEX and MYR had very intense fluorescence, good spot coverage with defined edges; HEX>MYR>>KE>E100.
- H50-8 chip: E100 and KE showed some fluorescence; E100>KE>>HEX>MYR.

The results indicate that strong binding can be achieved when the surface charge of the microparticle is made opposite in sign to the charge on the chip. Thus, the anionic surfactant-coated particles in sample "KE" bound strongly to the quaternary ammonium functionalized "Q-10" chip, and the cationic surfactant-coated particles in samples "MYR" and "HEX" bound strongly to the carboxylated "CM10-8" chip. The latter result in particular indicates the utility of the double-coating approach, since the particle surface prior to the second coating is negative (approximately −10 mV zeta potential for the zinc-NAT coated particles). It is also important to note that singly-coated (zinc-NAT only) particles bound moderately to the cationic Q-10 chips, due to their mildly anionic zeta potential.

Example 3

An L2 phase containing the anesthetic propofol was first prepared in a 100 mL test tube by mixing 0.302 grams of propofol (Albemarle Corporation, Baton Rouge, La.), 0.272 gm of vitamin E (Archer Daniels Midland Co., Decatur Ill.), and 1.653 gm of Pluronic L122 (Ethox Chemicals, Greenville, S.C.). Next, 0.162 gm of the anionic surfactant sodium deoxycholate (Aldrich Chemical Company, Milwaukee, Wis.) and 0.487 gm of glycine (Spectrum Chemical Company, Gardena, Calif.) were dissolved in 29.352 gm of distilled water. Then, 27.797 gm of the surfactant solution was added to the 100 mL test tube containing the propofol L2 phase. Upon contact with water, a reversed cubic phase was formed and subsequently dispersed using a homogenizer (Brinkman Polytron PT 3000) at 29 k rpm for 10 minutes. The dispersion was filtered using a 0.22 μm PVDF syringe filter (Millipore, Ireland). Observation in a Reichert-Jung Polyvar microscope operating in differential interference contrast (DIC) mode demonstrated that a particle size on the order of 200 nanometers had been achieved. This dispersion of uncoated particles was referred to as PF1112304 L2.

Example 4

The components of a reversed cubic phase containing the local anesthetic bupivacaine were combined in a 50 mL test tube by first dissolving 0.454 grams of free base bupivacaine in 1.829 gm of Vitamin E (Archer Daniels Midland Co, Decatur Ill.) and heating to 60° C. The free base bupivacaine was prepared by dissolving 25.019 gm of bupivacaine HCl monohydrate (Spectrum Chemical Company, Gardena, Calif.) in 600 mL of distilled water, then adding a 70 mL of 1.0N NaOH (Spectrum Chemical Company, Gardena, Calif.), decanting off the liquid, and drying the free base bupivacaine using a RotoVap (Polyscience, Niles, Ill.) with 30 mBar vacuum (BrandTech Scientific, Essex, Conn.) applied for 4 hours. Following dissolution of bupivacaine in vitamin E, 0.919 gm of sterile water and 1.831 gm of warm (40° C.) Pluronic P123 (BASF, Greenville, S.C.) were added to the test tube. Next, 12.445 gm of a diethanolamine-NAT solution was added to the 50 mL test tube containing the cubic phase components. The diethanolamine-NAT solution was prepared by mixing 3.148 gm of diethanolamine (Aldrich Chemical Company, Milwaukee, Wis.), 7.364 gm of distilled water, and 4.505 gm of N-acetyl-DL-tryptophan (MP Biomedicals, Aurora, Ohio). The cubic phase/diethanolamine-NAT mixture was homogenized (Brinkmann Polytron PT3000) at 29.5 k rpm for two minutes. While the material was being homogenized, 0.643 gm of diethanolamine and 9.489 gm of a 16.6% wt/wt zinc acetate solution (Sigma Chemical Company, St. Louis, Mo.) were added. Homogenizing continued for five minutes, and then the mixture was quickly transferred to a microfluidizer (Microfluidics M110 L) where 8 runs of 1.5 minutes each at 18 kspi were performed. Next, 1.1 mL of hot (60° C.) 6% wt/wt sorbitan monopalmitate dispersion (Spectrum Chemical, Gardena, Calif.) and 1.1 mL of 15% wt/wt aqueous albumin solution (Sigma Chemical Company, St. Louis, Mo.) were added while microfluidizing. Following 4 more microfluidizing runs of 1.5 minutes each, the dispersion was pumped out and allowed to sit overnight. The following day, 4 more microfluidizing runs of 1.5 minutes were completed. The dispersion was then divided into 6 centrifuge tubes of 3.5 mL of dispersion each. Approximately 0.14 gm of GAC 830 Activated Carbon (Norit, Atlanta, Ga.) was added to each tube and the tubes were agitated at 100 rpm for 15 minutes on a shaker (Lab-line Junior Orbit Shaker). Each tube was then centrifuged (Clay Adams compact physicians centrifuge) for 5 minutes at 4800 rpm. The top phase was pipetted off and filtered using a 5 µm PVDF syringe filter (Millipore, Ireland). This dispersion was labelled "F2V102604 top phase".

An important aspect of this Example is the fact that uncoated particles were converted to coated particles (coated by the zinc salt of NAT) by the addition of zinc acetate.

Example 5

A reversed cubic phase was prepared by first dissolving 0.040 grams of egg yolk ovomucoids (Belovo SA, Inc, Belgium) in 1.036 gm of a 20 mM sodium acetate, 0.5% sodium chloride, pH 4 buffer solution; the latter prepared by dissolving 0.272 gm of sodium acetate (Spectrum Chemical, Gardena, Calif.) and 0.500 gm of sodium chloride (EM Science, Gibbstown, N.J.) in 100 mL of distilled water and adjusting the pH to 4 with 1M hydrochloric acid (Sigma Chemical Company, St. Louis, Mo.). Next, 1.504 gm Vitamin E (Archer Daniels Midland Co, Decatur Ill.) and 2.399 gm of Pluronic L122 (Ethox Chemicals, Greenville, S.C.) were added. After thorough mixing, the material was optically isotropic and of high viscosity. Of this, 4.005 gm of cubic phase was combined in a 100 mL test tube with 10.049 gm of a diethanolamine-NAT; the latter prepared by mixing 5.248 gm of diethanolamine (Aldrich Chemical Company, Milwaukee, Wis.), 12.273 gm of distilled water, and 7.505 gm of N-acetyl-DL-tryptophan (MP Biomedicals, Aurora, Ohio). The cubic phase/diethanolamine-NAT mixture was first vortexed, then homogenized (Brinkman Polytron PT3000) at 29.5 k rpm for two minutes. While the material was being homogenized, 0.553 gm of diethanolamine and 7.547 gm of a 16.6% wt/wt zinc acetate solution were added. Homogenizing continued for five minutes, and then 0.8 mL of hot (60° C.) 6% wt/wt so/titan monopalmitate dispersion (Spectrum Chemical, Gardena, Calif.) and 0.8 mL of 15% wt/wt aqueous albumin solution (Sigma Chemical Company, St. Louis, Mo.) were added. Following five more minutes of homogenizing, the dispersion was divided into 6 centrifuge tubes of 3.5 mL of dispersion each. Approximately 0.14 gm of GAC 830 Activated Carbon (Norit, Atlanta, Ga.) was added to each tube and the tubes were agitated at 100 rpm for 15 minutes on a shaker (Lab-line Junior Orbit Shaker). Each tube was then centrifuged (Clay Adams compact physicians centrifuge) for 5 minutes at 4800 rpm. The top phase was pipetted off and saved as "Lyotropic/IC2 BLANK."

A 10% solution of the cationic polymer Eudragit E100 was prepared by mixing 0.504 gm of Eudragit E100 (Rohm Pharma Polymers, Germany), 0.500 gm of lactic acid (Johnson Matthey, Ward Hill, Mass.), and of 4.013 gm distilled water. A 10% dispersion of the anionic surfactant K. Emplex was prepared by mixing 0.5016 gm of K. Emplex (American Ingredients Co., Grandview, Mo.) and 4.505 gm of distilled water. The 10% K. Emplex dispersion was vortexed and heated to 75° C. In separate 8 mL test tubes, 0.5/mL of 10% Eudragit E100 solution was added to 4.502 gm of "Lyotropic/IC2 BLANK" and 1.0 mL of hot 10% K; the result was named "IC2102604 1% eudragit E100". Emplex dispersion was added to 4.002 gm of "Lyotropic/IC2 BLANK", and the resulting dispersion named "IC2102604 2% K Emplex" (or "IC2-KE"). The mixtures were immediately vortexed to disperse.

Example 6

In this experiment, various embodiments of the current invention were used as blocking agents in an ELISA experiment, to determine the degree to which the particles bound to the substrate and blocked the adsorption of an antibody.
Reagents and materials used:
1. Phosphate-buffered saline (PBS): 150 mM NaCl, 150 mM $Na_2HPO_4/NaH_2PO_4$ pH 7.2
2. BSA: 1% bovine serum albumin (Sigma A7906) in PBS
3. Ab-HRP conjugate: monoclonal anti-goat IgG—peroxidase (Sigma A9452, approx 6.5 mg/ml) diluted 1:10,000 in PBS
4. Stop soln: 0.5 M $H_2SO_4$
5. TMB: Sigma T8665, a peroxidase substrate solution based on tetramethylbenzidine
6. ELISA plates: Nalge Nunc 96 well high flange, 300 ul capacity, uncoated polystyrene Four embodiments of the current invention were used:
L1: F2V102804 prepared as described in Example 4
L2: PF1112304 L2 prepared as described in Example 3
L3: IC2102604 1% eudragit E100 prepared as described in Example 5
L4: IC2102604 2% K emplex prepared as described in Example 5

The procedure used was as follows.
1. Into an ELISA well, pipette 300 ul of preparation & incubate 10 minutes at room temperature:

| well | content |
| --- | --- |
| 1-4 | PBS |
| 5-8 | BSA |
| 9-12 | L1 |
| 13-16 | L2 |
| 17-19 | L3 |
| 21-23 | L4 |

2. Aspirate well contents, add 300 ul PBS, aspirate contents & blot dry.
3. Add to each well 50 ul Ab-HRP conjugate. Incubate 20 minutes at room temperature.
4. Aspirate well contents followed by 2×300 ul PBS rinses. Blot dry.
5. Add 50 ul TMB, incubate 10 minutes room temperature.
6. Add 50 ul Stop solution.
7. Photograph ELISA plate.
8. Combine contents of replicate wells and dilute 1:10 with 50% PBS/50% Stop soln.
Measure A450 (absorbance at 450 nm) versus PBS blank.
Results. The results are shown in the following chart:

| Blocking Preparation | A450 |
| --- | --- |
| PBS | 1.9630 |
| BSA | 0.2420 |
| F2V102804 top phase | 0.0680 |

| Blocking Preparation | A450 |
|---|---|
| PF1112304 L2 | 0.2090 |
| IC2102604 1% eudragit E100 | 0.0570 |
| IC2102604 2% K emplex | 0.0510 |

Thus, three coated particle preparations of the instant invention—IC2102604 1% eudragit, IC2102604 2% K-Emplex, both doubly-coated, and the singly-coated F2V 102804—exhibited greater polystyrene blocking capability than the standard blocking preparation of 1% bovine serum albumin. Preparation PF1112304 of uncoated particles exhibited slightly better blocking than BSA.

Example 7

The K-Emplex-coated (anionic surface) particle sample, here termed "I2-KE", produced in Example 1, and thus loaded with insulin, was selected for SELDI experiments using positively-charged "Q-10" chips. The procedure to prepare the SELDI chips in all the Examples reported herein was as follows, with Steps 2-6 accomplished by the robotics.
Step 1: Dilute the particle dispersion in 50 mM buffer, pH 7.4;
Step 2: Pretreat chips with buffer, 5 minutes×2;
Step 3: Add 25 ul of diluted sample to each Bioprocessor well;
   Incubate 30 minutes at room temperature;
Step 4: Wash chips 4× with 150 ul of buffer with 10 mixing cycles;
   Wash chips 1× with water;
Step 5: Remove Bioprocessor. Air dry chips for 10 minutes;
Step 6: Add (microliter of SPA matrix in 50% acetonitrile/water 0.5% TFA;
   Air dry for 15 minutes;
   Repeat matrix application;
   Air dry for 15 minutes before reading.
In this case, the "12-KE" dispersion was diluted by a factor of 1:1000, in Step 1. The chips were analyzed in a Ciphergen SELDI-MS instrument.
Results.
The following table shows the standard deviation, and the coefficient of variation, for each peak registered, before and after normalizing the m/z ratio based on the insulin standard. The results are depicted graphically in FIG. 5.

| m/z | | | | | |
|---|---|---|---|---|---|
| Before | | | After | | |
| Mean | SD | % CV | Mean | SD | % CV |
| 3450.331 | 1.428905 | 0.041% | 3450.331 | 0.543094 | 0.016% |
| 3899.16 | 1.838274 | 0.047% | 3899.16 | 0.850905 | 0.022% |
| 4160.347 | 1.943068 | 0.047% | 4160.347 | 0.416087 | 0.010% |
| 4187.138 | 3.866138 | 0.092% | 4187.139 | 5.216812 | 0.125% |
| 4255.586 | 2.16548 | 0.051% | 4255.586 | 1.222404 | 0.029% |
| 4364.707 | 1.869249 | 0.043% | 4364.707 | 0.275111 | 0.006% |
| 4476.072 | 1.933504 | 0.043% | 4476.072 | 0.163337 | 0.004% |
| 4634.313 | 2.027874 | 0.044% | 4634.313 | 0.187323 | 0.004% |
| 5743.398 | 2.565501 | 0.045% | 5743.398 | 0 | 0.000% |
| 6235.33 | 3.024563 | 0.049% | 6235.33 | 0.460464 | 0.007% |
| 6442.225 | 3.02608 | 0.047% | 6442.225 | 0.273127 | 0.004% |
| 6640.382 | 3.047743 | 0.046% | 6640.382 | 0.204372 | 0.003% |
| 6890.079 | 3.366266 | 0.049% | 6890.079 | 0.418004 | 0.006% |
| 6930.184 | 3.417675 | 0.049% | 6930.184 | 0.395398 | 0.006% |
| 6949.548 | 3.535925 | 0.051% | 6950.034 | 0.366776 | 0.005% |
| 7625.439 | 3.641834 | 0.048% | 7625.439 | 0.407421 | 0.005% |
| 7774.885 | 3.819105 | 0.049% | 7774.884 | 0.435893 | 0.006% |
| 8214.542 | 4.178585 | 0.051% | 8214.072 | 0.587112 | 0.007% |
| 8573 | 4.139301 | 0.048% | 8573 | 0.678145 | 0.008% |
| 8700.976 | 4.334909 | 0.050% | 8700.976 | 0.669145 | 0.008% |
| 8778.434 | 4.622205 | 0.053% | 8778.433 | 0.887131 | 0.010% |
| 8924.732 | 4.548431 | 0.051% | 8924.731 | 0.768855 | 0.009% |
| 9140.543 | 4.652185 | 0.051% | 9140.543 | 0.755525 | 0.008% |
| 9430.05 | 4.863498 | 0.052% | 9430.05 | 0.839832 | 0.009% |
| 9649.338 | 5.012949 | 0.052% | 9649.338 | 2.016245 | 0.021% |
| 9719.936 | 5.048652 | 0.052% | 9719.936 | 0.905098 | 0.009% |
| 12460.17 | 6.748364 | 0.054% | 12460.17 | 1.523945 | 0.012% |
| 12616.58 | 6.768427 | 0.054% | 12616.58 | 1.475958 | 0.012% |
| 13769.23 | 7.617153 | 0.055% | 13769.23 | 2.132805 | 0.015% |
| 13855.5 | 6.067183 | 0.044% | 13854.68 | 1.070892 | 0.008% |
| 13884.03 | 7.195736 | 0.052% | 13886.74 | 2.187885 | 0.016% |
| 15137.36 | 8.869256 | 0.059% | 15137.36 | 2.554225 | 0.017% |
| 15878.58 | 9.328144 | 0.059% | 15878.58 | 3.144241 | 0.020% |
| 17266.12 | 8.3904 | 0.049% | 17266.12 | 2.886141 | 0.017% |
| 17393.28 | 9.245409 | 0.053% | 17393.28 | 2.697426 | 0.016% |
| 17895.74 | 14.335 | 0.080% | 17898.42 | 13.67282 | 0.076% |
| 21509.6 | 6.305882 | 0.029% | 21511.43 | 5.648626 | 0.026% |
| 21776.09 | 8.866126 | 0.041% | 21780.64 | 4.279369 | 0.020% |
| 28067.07 | 14.04885 | 0.050% | 28069.45 | 6.282196 | 0.022% |
|  | 5.171893 | 0.051% |  | 1.782055 | 0.016% |

As can be seen, the standard deviation in peak position, calculated from eight repetitions, was reduced more than three-fold, from 5.17 (0.051% of mean) to 1.78 (0.016% of mean) by the use of this encapsulated insulin calibrant.

It should be noted that SELDI peaks registered for insulin in this, and other, experiments with the instant invention were in all cases of extremely high intensity, allowing very high dilutions (1:5000 and more) with the maintenance of a strong, sharp signal from the insulin. This indicates a strong propensity of the particles to achieve a high rate of deposition of the insulin onto the Q-10 chips, as well as other substrata.

Furthermore, the dispersion in this Example was tested for encapsulation of the insulin, in the following way. A centricon centrifuge filter was used to remove the particles from the aqueous exterior phase, and the latter was tested for insulin (un-encapsulated, or "free" insulin), using a standard ELISA assay. No free insulin was detected in this experiment, demonstrating a complete encapsulation of the peptide, an indication of the very high partition coefficient in the cubic phase interior over water.

Example 8

A dispersion of uncoated, anionically-charged cubic phase microparticles was first prepared. A reversed cubic phase containing AntiMouse IgG was prepared in an 8 mL test tube by combining 0.099 gm AntiMouse IgG (Sigma Chemical Company, St. Louis, Mo.) along with 0.229 gm sterile water (Abbott Labs, North Chicago, Ill.) and 0.470 gm vitamin E (Archer Daniels Midland Company, Decatur, Ill.). Lastly, 0.733 gm of Pluronic L122 (Ethox Chemicals, Greenville, S.C.) was added, and after thorough mixing the material was optically isotropic and of high viscosity. Of this, 1.220 gm of cubic phase was added to a 50 mL beaker into which had previously been dissolved 0.061 gm of deoxycholic acid, sodium salt (Aldrich Chemical Company, Milwaukee, Wis.) and 0.272 gm glycine (Spectrum Chemical, Gardena, Calif.) into 16.484 gm of sterile water. The cubic phase/aqueous solution was dispersed first with a Homogenizer (Brinkmann Polytron PT3000) at 29.5 k rpm for one minute, then with a Microfluidizer Processor (Microfluidics M110L) at 18 k psi for two runs of 1.5 minutes each. The sample was removed from the Microfluidizer and the pH measured at 7.4 (Hanna Instruments, Woonsocket, R.I.) before filtering through a 0.22 um PVDF syringe filter (Millipore Corporation, Bedford, Mass.). The sample was denoted "Lyotropic/AM1", or alternatively as "AM1 Lyocells".

This dispersion of uncoated cubic phase particles, which was denoted "AM1 LyoCells", was then tested for its effect on SELDI analysis of blood proteins. A 1:1000 dilution of this dispersion was added to serum from a normal (cancer-free) patient population, and the spiked plasma analyzed with a Ciphergen Q-star SELDI system employing cationic (anion-exchange) "Q-10" chips. The resulting mass spec data are shown graphically in FIG. 5; and numerically in the following table:

| Mean m/z | Buffer | % CV | I1 | % CV | AM1 | % CV |
|---|---|---|---|---|---|---|
| 3083.79 | 1.167 | 82.2% | — | | — | |
| 3443.05 | 5.337 | 28.2% | — | | — | |
| 3485.60 | 2.387 | 25.9% | — | | — | |
| 3815.55 | 1.689 | 63.4% | — | | — | |
| 3891.46 | 2.321 | 28.3% | 3.304 | 13.7% | 4.313 | 6.1% |
| 4151.86 | 41.087 | 5.4% | 49.931 | 8.6% | 63.588 | 7.4% |
| 4184.28 | 13.421 | 25.3% | 19.334 | 12.9% | 25.335 | 8.3% |
| 4245.32 | 3.958 | 40.5% | 5.129 | 7.9% | 6.658 | 9.3% |
| 4357.41 | 3.830 | 24.7% | 4.929 | 8.0% | 6.704 | 13.6% |
| 4467.30 | 4.022 | 23.4% | 5.005 | 9.5% | 6.859 | 10.3% |
| 4625.28 | 4.735 | 34.5% | 5.748 | 7.3% | 7.921 | 8.2% |
| 4708.90 | | | 3.626 | 4.7% | 4.233 | 8.1% |
| 5736.28 | | | 2.579 | 5.9% | | |
| 6224.72 | 1.347 | 62.2% | 2.010 | 19.6% | 2.150 | 20.4% |
| 6431.59 | 5.071 | 30.6% | 16.521 | 6.6% | 21.157 | 8.2% |
| 6629.53 | 11.053 | 32.5% | 29.316 | 5.9% | 37.997 | 7.8% |
| 6832.91 | | | | | 4.724 | 9.5% |
| 6879.07 | 5.713 | 38.9% | 8.691 | 7.6% | 11.094 | 5.7% |
| 6939.00 | 7.591 | 36.1% | 10.250 | 9.8% | 12.738 | 5.1% |
| 7613.94 | 4.216 | 20.1% | 4.886 | 8.0% | 6.354 | 6.1% |
| 7763.54 | 4.078 | 19.7% | 3.275 | 58.7% | 3.126 | 18.1% |
| 8201.88 | 0.920 | 11.5% | 2.445 | 8.4% | 3.314 | 12.1% |
| 8560.28 | | | 2.337 | 11.2% | 3.563 | 4.0% |
| 8687.14 | 2.195 | 31.1% | 5.758 | 5.0% | 8.875 | 6.4% |
| 8762.00 | | | 4.404 | 6.3% | 6.285 | 6.7% |
| 8807.26 | 1.853 | 44.0% | 4.903 | 1.4% | 7.103 | 6.4% |
| 8911.83 | 4.259 | 7.9% | 11.931 | 7.8% | 16.922 | 7.6% |
| 9127.65 | 3.330 | 19.9% | 11.524 | 6.3% | 16.290 | 9.3% |
| 9298.99 | 3.281 | 10.0% | | | | |
| 9416.53 | 7.001 | 19.0% | 23.128 | 6.4% | 30.925 | 6.6% |
| 9636.71 | 1.642 | 9.2% | 4.583 | 8.0% | 6.051 | 3.5% |
| 9706.07 | 2.719 | 17.5% | 8.371 | 8.9% | 10.822 | 6.9% |
| 9926.52 | | | 1.865 | 8.3% | | |
| 10066.3 | 0.782 | 27.8% | | | | |
| 10640.5 | 0.432 | 35.9% | | | | |
| 12444.4 | 5.049 | 56.5% | 6.970 | 15.1% | 9.022 | 14.4% |
| 12600.7 | 2.115 | 52.4% | 2.757 | 12.5% | 3.559 | 15.1% |
| 12833.9 | 0.763 | 40.1% | 1.045 | 8.2% | 1.487 | 2.6% |
| 13750.6 | 12.483 | 44.9% | 17.964 | 2.6% | 24.818 | 3.4% |
| 13872.1 | 15.965 | 39.6% | 20.797 | 3.2% | 28.968 | 6.1% |
| 14046.7 | 4.826 | 30.7% | 6.217 | 0.9% | 8.522 | 5.2% |
| 15116.4 | 0.622 | 8.1% | 0.606 | 14.4% | 0.716 | 7.1% |
| 15856.1 | 0.328 | 17.1% | 0.310 | 14.1% | 0.391 | 12.3% |
| 17125.8 | | | 1.108 | 8.9% | 1.839 | 11.9% |
| 17244.9 | 1.002 | 26.4% | 2.364 | 9.3% | 4.042 | 12.6% |
| 17371.2 | 1.030 | 26.3% | 2.442 | 8.1% | 4.116 | 12.6% |
| 17862.9 | 0.268 | 17.0% | 0.615 | 7.9% | 1.019 | 3.6% |
| 18315.8 | | | 0.314 | 8.3% | 0.848 | 6.9% |
| 18602.4 | | | | | 0.499 | 13.0% |
| 21025.0 | | | | | 0.323 | 11.1% |
| 21485.2 | 0.265 | 21.0% | 0.267 | 4.4% | 0.364 | 18.5% |
| 21754.4 | 0.276 | 13.1% | 0.239 | 6.0% | 0.333 | 21.6% |
| 22256.9 | 0.272 | 81.7% | | | | |
| 23174.5 | | | 0.287 | 7.7% | 0.420 | 24.3% |
| 26301.6 | 0.061 | 29.3% | | | | |
| 28038.0 | 1.425 | 25.8% | 2.288 | 8.9% | 3.858 | 22.4% |
| 28825.0 | | | | | 0.829 | 28.8% |
| 31091.3 | | | 0.167 | 2.6% | 0.230 | 12.7% |
| 33340.7 | 1.183 | 103.0% | | | 0.293 | 25.1% |
| 33528.8 | | | 0.233 | 11.7% | 0.280 | 26.2% |
| 33838.1 | 0.794 | 84.2% | 0.230 | 10.3% | | |
| 33946.7 | | | 0.230 | 10.3% | | |
| 37019.3 | | | | | 0.116 | 34.5% |
| 37245.5 | | | | | 0.122 | 16.6% |
| 37392.2 | | | 0.071 | 7.7% | 0.127 | 22.9% |
| 38713.5 | 0.106 | 42.3% | 0.125 | 19.6% | 0.184 | 38.1% |

Figure 5:
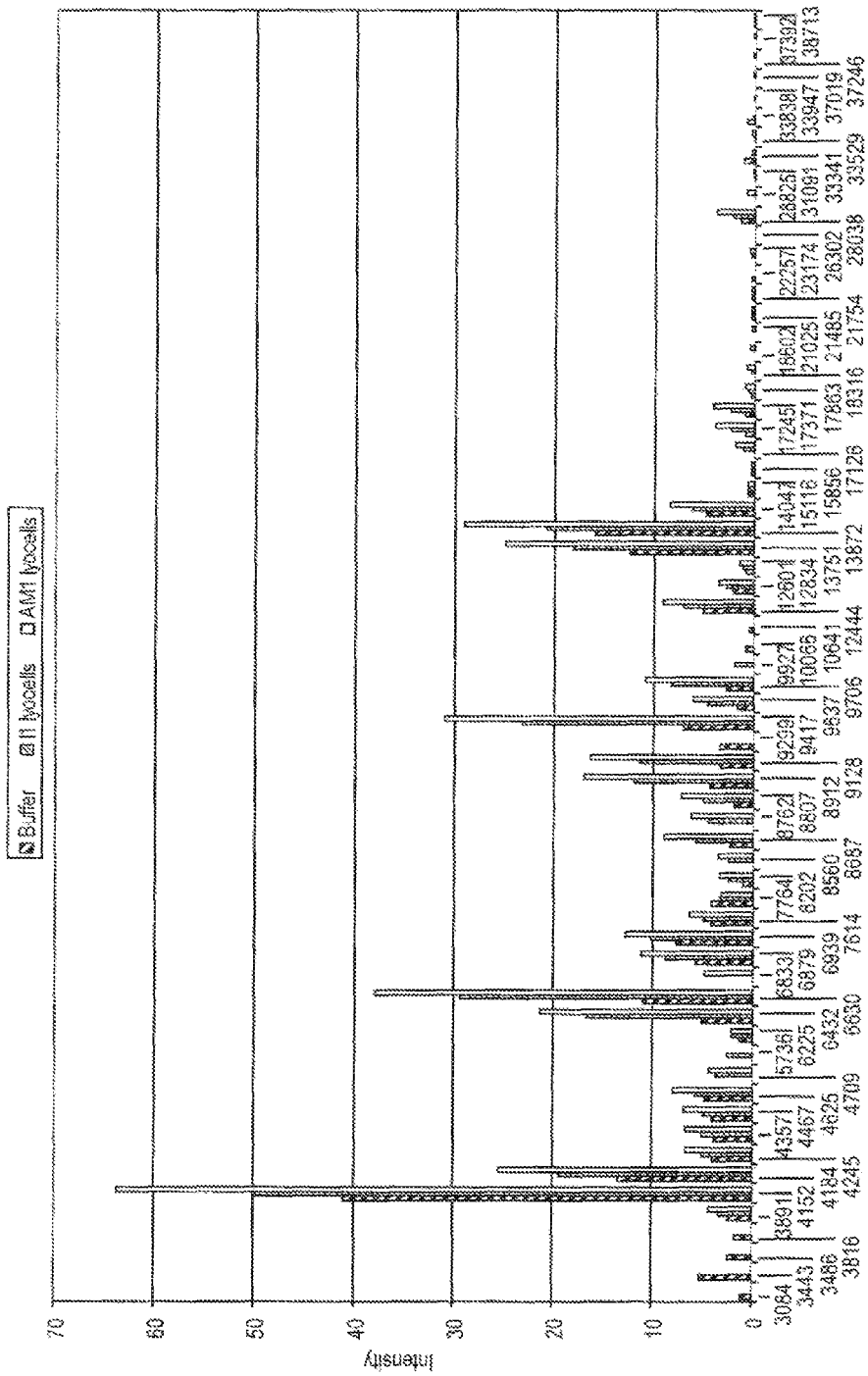
FIG. 5. As discussed in Example 8, a plot of mass, spec intensities as a function of the molecular mass to charge (m/z) ratio, for biomacromolecules in a pool of serum from normal (cancer-free) human subjects. Three preparations are plotted for each m/z. The left-most bar (solid) at each ratio is the case where serum was added to a simple buffer, and the right-most bar (hollow) is the case where serum was added to a buffer-diluted (1:1000) dispersion of coated reversed cubic phase particles of material.

Several conclusions can be drawn from the FIG. 5. First, intensities are clearly and consistently increased in the presence of cubic phase particle dispersion AM1 (and to a lesser extent with another cubic phase preparation, "I1"), as is the signal-to-noise ratio, and this is true for essentially every peak registered. Secondly, some proteins that were not registered in the absence of the particles, were detected in the presence of the AM1 LyoCell particles. For example, a moderately strong peak at about m/z=6833 is clearly registered with "AM1" particles present, even though it is not detectable without the particles present. Obviously the cubic phase particles are binding well to the Q-10 chips, presumably by virtue of their anionic charge, with the implication that any proteins absorbed by, or adsorbed to, the particles will be brought down to the surface—in some cases, at least, when they would not normally bind to the substrate. And third, the coefficient of variation (CV) is dramatically lower in the presence of the cubic phase dispersions than in the absence thereof. This strong effect of decreasing the variability of the measurement is not simply the non-specific effect of surfactant, since it was not seen when Triton-X was added in place of the cubic phase particles.

Notwithstanding the appearance of new peaks, the overall spectra with and without particles are very similar with the main effect being amplification of the signal, and greatly reducing the variability. It is quite likely that the particles are bringing down to the substrate a rich concentration of proteins, increasing the number of anionic proteins reaching (and binding to) the substrate, but that proteins which are cationic at this pH nevertheless desorb in the course of the experiment, and new peaks which appear in the presence of the particles are most likely those which are uncharged or weakly charged (that is, near their isoelectric point). Tentatively at least, one can draw the following conclusions from these data:

1) these particles can significantly improve the signal strength and signal-to-noise ratio of the registered peaks;
2) for the most part, the selectivity obtained by the use of a SELDI substrate is retained, in the presence of the particles;
3) likely, it is possible to identify proteins near their isoelectric point, by noting those peaks that appear in the presence of the particles but not in their absence.

Example 9

A dispersion of doubly-coated particles loaded with both bovine insulin and beta-casein, with an outer coating of Eudragit E100, was first prepared as follows. A reversed cubic phase containing the proteins insulin and beta-casein was prepared by first dissolving 0.048 grams of egg yolk phospholipids (Belovo SA, Inc, Belgium) in 1.251 gm of a 20 mM sodium acetate, 0.5% sodium chloride, pH 4 buffer solution;

the latter prepared by dissolving 0.272 gm of sodium acetate (Spectrum Chemical, Gardena, Calif.) and 0.500 gm of sodium chloride (EM Science, Gibbstown, N.J.) in 100 mL of distilled water and adjusting the pH to 4 with 1M hydrochloric acid (Sigma Chemical Company, St. Louis, Mo.). Next, 0.016 gm insulin from bovine pancreas and 0.015 gm beta-casein (both from Sigma Chemical Company, St. Louis, Mo.) were added to the buffer solution, and 0.001 gm rhodamine B base (Aldrich Chemical Company, Milwaukee, Wis.) added. Finally, 1.803 gm vitamin E (Archer Daniels Midland Company, Decatur, Ill.), and 2.888 gm of Pluronic L122 (Ethox Chemicals, Greenville, S.C.) were added. After thorough mixing the material was optically isotropic and of high viscosity. Of this, 4.999 gm of cubic phase was combined in a 50 mL beaker with 12.478 gm of a diethanolamine-NAT solution; the latter prepared by mixing 3.151 gm of diethanolamine (Aldrich Chemical Company, Milwaukee, Wis.), 7.358 gm of distilled water, and 4.503 gm of N-acetyl-DL-tryptophan (MP Biomedicals, Aurora, Ohio). The cubic phase/diethanolamine-NAT mixture was dispersed with a Homogenizer (Brinkmann Polytron PT3000) at 29.5 k rpm for three minutes. To the homogenizer was then added 0.599 gm of diethanolamine and 9.441 gm of a 16.6% wt/wt zinc acetate solution. Homogenizing at 29.5 k rpm was continued for five minutes, and then 1.1 mL of hot (60° C.) 6% wt/wt sorbitan monopalmitate dispersion (Spectrum Chemical, Gardena, Calif.) and 1.1 mL of 15% wt/wt aqueous albumin solution (Sigma Chemical Company, St. Louis, Mo.) were added. Following five additional minutes of homogenizing, 4.5 mL of dispersion was placed into each of 6 centrifuge tubes containing approximately 0.14 gm of GAC 830 Activated Carbon (Norit, Atlanta, Ga.) and the tubes were agitated at 100 rpm for 15 minutes on a shaker (Lab-line Junior Orbit Shaker). Each tube was then centrifuged (Clay Adams compact physicians centrifuge) for 5 minutes at 4800 rpm. The top phase was saved as "Lyotropic/IC2."

This dispersion was then tested in a SELDI analysis of blood plasma proteins, employing the cationic "Q-10" chips from Ciphergen. Insulin, with a MW of approximately 5743.5 and beta-casein at approximately 24,075 were both registered even when the dispersion was diluted by 1:5000 in Step 1 of the procedure described above. Averaging two runs at each of 4 dilutions, the intensities of these two peaks were as follows:

|  | Dilution | | | |
| --- | --- | --- | --- | --- |
|  | 1:500 | 1:1000 | 1:2500 | 1:5000 |
| Insulin intensity | 40.4 | 17.0 | 7.1 | 5.3 |
| Casein intensity | 0.08 | 0.03 | 0.02 | 0.03 |

Thus, a single particle loaded with two proteins has yielded two peaks, corresponding to the two proteins, in this SELDI-MS experiment.

Example 10

Antibody was incorporated in uncoated cubic phase particles in this Example and shown to bind to an ELISA plate, and subsequently to bind a second antibody much more strongly than control particles without the first antibody. The experiment also demonstrates the strong NSB-blocking property of the particles.

A reversed cubic phase containing AntiMouse IgG was prepared in an 8 mL test tube by combining 0.055 gm Anti-Mouse IgG (Sigma Chemical Company, St. Louis, Mo.) along with 0.662 gm Patchouli Oil (Aura Cacia, Norway, Iowa), 0.080 gm dimyristoyl phosphatidylglycerol (NOF, Tokyo, Japan) and 0.434 gm of a 6% deoxycholic acid, sodium salt (Aldrich Chemical Company, Milwaukee, Wis.) solution. Lastly, 0.822 gm of phosphatidylcholine (Avanti Polar Lipids, Alabaster, Ala.) was added, and after thorough mixing the material was optically isotropic and of high viscosity. Of this, 1.366 gm of cubic phase was added to a 50 mL beaker into which had previously been dissolved 0.101 gm glycine (Spectrum Chemical, Gardena, Calif.) into 18.512 gm of distilled water. Three drops of 1N NaOH (Spectrum Chemical, Gardena, Calif.) were added before the cubic phase/aqueous solution was dispersed, first with a Homogenizer (Brinkmann Polytron PT3000) at 29.5 k rpm for one minute, then with a Microfluidizer Processor (Microfluidics M110L) at 18 k psi for two runs of 1.5 minutes each. The sample was removed from the Microfluidizer and the pH measured at 7.8 (Hanna Instruments, Woonsocket, R.I.) before filtering through a 0.45 um PVDF syringe filter (Millipore Corporation, Bedford, Mass.). The sample was saved as "Lyotropic/AM5011405." Similar samples with no protein, and with albumin in place of the antibody, were also prepared.

The reagents and substrate used in the experiment were as follows:
1. Antibody1: rabbit anti-mouse IgG (Sigma M7023, Lot 083K4837, 2.8 mg/ml) 1:5,000 in PBS.
2. Antibody2: mouse anti-goat IgG-HRP conj (Sigma A9452, Lot 023K4819, 6.5 mg/ml) 1:5,000 in PBS.
3. Tetramethylbenzidine (TMB): Sigma T8665.
4. Stop soln: 0.5N sulfuric acid.
5. ELISA plates: Nalge NUNC 96 well high plane, uncoated polystyrene 300 μl capacity.
6. PBS: 0.01M phosphate, 0.138 M NaCl 0.0027M KCl pH7.4 Sigma P3813).
Uncoated cubic phase particle preparations, with L1 and L2 being the blanks, and L3 the "live" antibody-containing dispersion:
L1: blank, uncoated, phosphatidylcholine/patchouli/deoxycholate, no protein (AM5012005).
L2: blank, uncoated, PC/patchouli/deoxycholate with albumin at 2.3 μg/ml (AM5012005).
L3: blank, uncoated, PC/patchouli/deoxycholate with antibody1 at 4.6 μg/ml (AM5011405).
Procedure:
1. Pipette 300 μL PBS or cubic phase preparation into quadruplicate ELISA wells, incubate 20 minutes at RT, according to the following (herein the term "lyocells" refers to a dispersion of cubic phase particles):

| Sample | Contents | Comments |
| --- | --- | --- |
| C0 | PBS | control |
| C1 | L1 | blank lyocell |
| C2 | L2 | lyocell + albumin |
| S1 | L3 | lyocell + Antibody1 |
| S2 | L3/C1 | 1:10 dilution of S1 into buffer |
| S3 | L3/C1 | 1:10 dilution of S2 into buffer |
| S4 | L3/C1 | 1:10 dilution of S3 into buffer |
| S5 | L3/C2 | 1:10 dilution of S1 into blank lyocells |
| S6 | L3/C2 | 1:10 dilution of S5 into blank lyocells |
| S7 | L3/C2 | 1:10 dilution of S6 into blank lyocells |
| S1-3X | L3 | S1 washed 3× at step 2 |
| S2-3X | L3/C1 | S2 washed 3× at step 2 |
| S3-3X | L3/C1 | S3 washed 3× at step 2 |
| S4-3X | L3/C1 | S4 washed 3× at step 2 |
| S5-3X | L3/C2 | S5 washed 3× at step 2 |

-continued

| Sample | Contents | Comments |
|--------|----------|----------|
| S6-3X | L3/C2 | S6 washed 3x at step 2 |
| S7-3X | L3/C2 | S7 washed 3x at step 2 |

2. Aspirate well contents & wash w/300 µL PBS & blot
3. Pipette 50 µL Antibody2 (conjugate). Incubate 30 min RT
4. Aspirate well contents & wash w/300 µL PBS & blot
5. Pipette 100 µL TMB solution & incubate 15 min RT
6. Pipette 200 µL stop solution.
7. Combine 200 µl of 2 representative wells and read A450
Results:

| Sample | Description | A450 |
|--------|-------------|------|
| C0 | PBS buffer | >3.0 |
| C1 | naked lyocells – no protein | 0.188 |
| C2 | naked lyocells + albumin | 0.213 |
| S1 | naked lyocell + antibody | 0.655 |
| S2 | S1 diluted 1:10 w/PBS | 0.245 |
| S3 | S2 diluted 1:10 w/PBS | 0.546 |
| S4 | S3 diluted 1:10 w/PBS | >3.0 |
| S5 | S1 diluted 1:10 w/C2 | 0.308 |
| S6 | S5 diluted 1:10 w/C2 | 0.187 |
| S7 | S6 diluted 1:10 w/C2 | 0.183 |
| S1-3X | S1 w/3x wash | 0.484 |
| S2-3X | S2 w/3x wash | 0.211 |
| S3-3X | S3 w/3x wash | 0.452 |
| S4-3X | S4 w/3x wash | >3.0 |
| S5-3X | S5 w/3x wash | 0.228 |
| S6-3X | S6 w/3x wash | 0.172 |
| S7-3X | S7 w/3x wash | 0.192 |

Thus, the antibody-containing lyocells demonstrated more capacity to bind the conjugate that either the blank or albumin-containing lyocells. In addition, all preparations showed very strong NSB-blocking capacity relative to buffer.

Serial dilution of antibody-containing lyocell with blank lyocells demonstrated a dose-response. If the lyocell-coated wells were washed three times instead of once (before conjugate is added), some of the binding capacity was eliminated.

Example 11

In this Example, a preparation of insulin-containing cubic phase particles as described above was shown to deposit insulin effectively on a traditional ELISA substrate, and the insulin was then detected in an ELISA assay.
Reagents Used:
Antibodies (all dilutions made with PBS):
anti-hCG monoclonal (Fitzgerald clone M94138) as a Control
    diluted 1:200 (final conc.=5 µg/mL)
    and 1:2000 (final conc.=0.5 µg/mL)
anti-Insulin monoclonal from Abcam (clone ab7760)
    diluted 1:100 (final conc=1 µg/mL)
    diluted 1:1000 (final conc.=0.1 µg/mL)
Protocol
E100 doubly-coated cubic phase particles containing Insulin were diluted 1/10 in Phosphate Buffer (pH 7.6), and in Carbonate Buffer (pH 8.5). All wells coated overnight at 4° C. (100 µL/well), then rinsed with PBS then blocked with SuperBlock 1 hour (300 µL/well), and again rinsed 3x with PBS. Mouse anti-insulin monoclonal antibodies added and incubated for 1 hour (100 µL/well). The wells were then rinsed 5x with PBS. Goat anti-mouse HRP conjugate was then added (1:2500 dilution) incubated for 1 hour (100 µL/well), after which the wells were rinsed 5x with PBS. HRP substrate was finally added (100 µL/well), and the reaction stopped with 0.1 M HCl (100 µL/well).
Results.
The optical densities (OD) in the wells read as follows:

|  | Phosphate Buffer OD 450 | Mean | Carbonate Buffer OD 450 | Mean |
|---|---|---|---|---|
| Blank | 0.055 | 0.055 | 0.054 | 0.053 |
|  | 0.054 |  | 0.051 |  |
| anti-hCG (500 ng) | 0.060 | 0.067 | 0.063 | 0.065 |
|  | 0.074 |  | 0.066 |  |
| anti-hCG (50 ng) | 0.061 | 0.058 | 0.061 | 0.070 |
|  | 0.054 |  | 0.078 |  |
| anti-Insulin (100 ng) | 0.715 | 0.743 | 0.710 | 0.723 |
|  | 0.761 |  | 0.735 |  |
|  | 0.754 |  | 0.725 |  |
| anti-Insulin (10 ng) | 0.705 | 0.705 | 0.676 | 0.687 |
|  | 0.701 |  | 0.697 |  |
|  | 0.709 |  | 0.687 |  |

The high optical densities in the anti-insulin cases show that the insulin was successfully deposited and accessible on the substrate, and the low OD in the anti-HCG control shows that the binding was specific for insulin/anti-insulin binding.

Example 12

A reversed cubic phase was prepared by combining 1.005 gm deionized water (Spectrum Chemical, Gardena, Calif.), 1.000 gm Carvone (Aldrich Chemical Company, Milwaukee, Wis.), 0:251 gm Strawberry Aldehyde (Penta Manufacturing, Livingston, N.J.), 0.257 gm Sandalwood Oil (Cedar Vale, Cedar Vale, Kans.) and 2.509 gm of Pluronic L122 (Ethox Chemicals, Greenville, S.C.). After thorough mixing the material was optically isotropic and of high viscosity. Of this, 4.609 gm of cubic phase was combined in a 50 mL beaker with 13.399 gm of a diethanolamine-NAT solution; the latter prepared by mixing 3.746 gm of diethanolamine (Aldrich Chemical Company, Milwaukee, Wis.), 6.746 gm of distilled water, and 4.495 gm of N-acetyl-DL-tryptophan (MP Biomedicals, Aurora, Ohio). The cubic phase/diethanolamine-NAT mixture was dispersed with a Homogenizer (Brinkmann Polytron PT3000) at 15 k rpm for five minutes. The homogenizer speed was then reduced to 5 k rpm and to it was added 1.001 gm of 1% Fluorescent-Labeled Albumin (FITC-albumin, Sigma Chemical Company, St. Louis, Mo.) and homogenizing continued for two minutes. After the sample was allowed to sit undisturbed for 20 minutes, 9.100 gm of a 20% wt/wt zinc acetate solution was slowly added while stirring on a stir plate. When magnetic stirring became impossible due to increased viscosity, the dispersion was hand-stirred with a spatula. The pH was measured to be 8.2 (Hanna Instruments, Woonsocket, R.I.). The sample was divided into two test tubes and centrifuged (Clay Adams compact physicians centrifuge) for 60 minutes at 4800 rpm, and the top, liquid phase, representing the exterior phase to the particles, was examined to determine whether the fluorescent protein had been taken up by the particles. To facilitate this, a control sample was prepared by mixing the same total amount of FITC-albumin into the same amount of water as in the dispersion.

Figure 6:
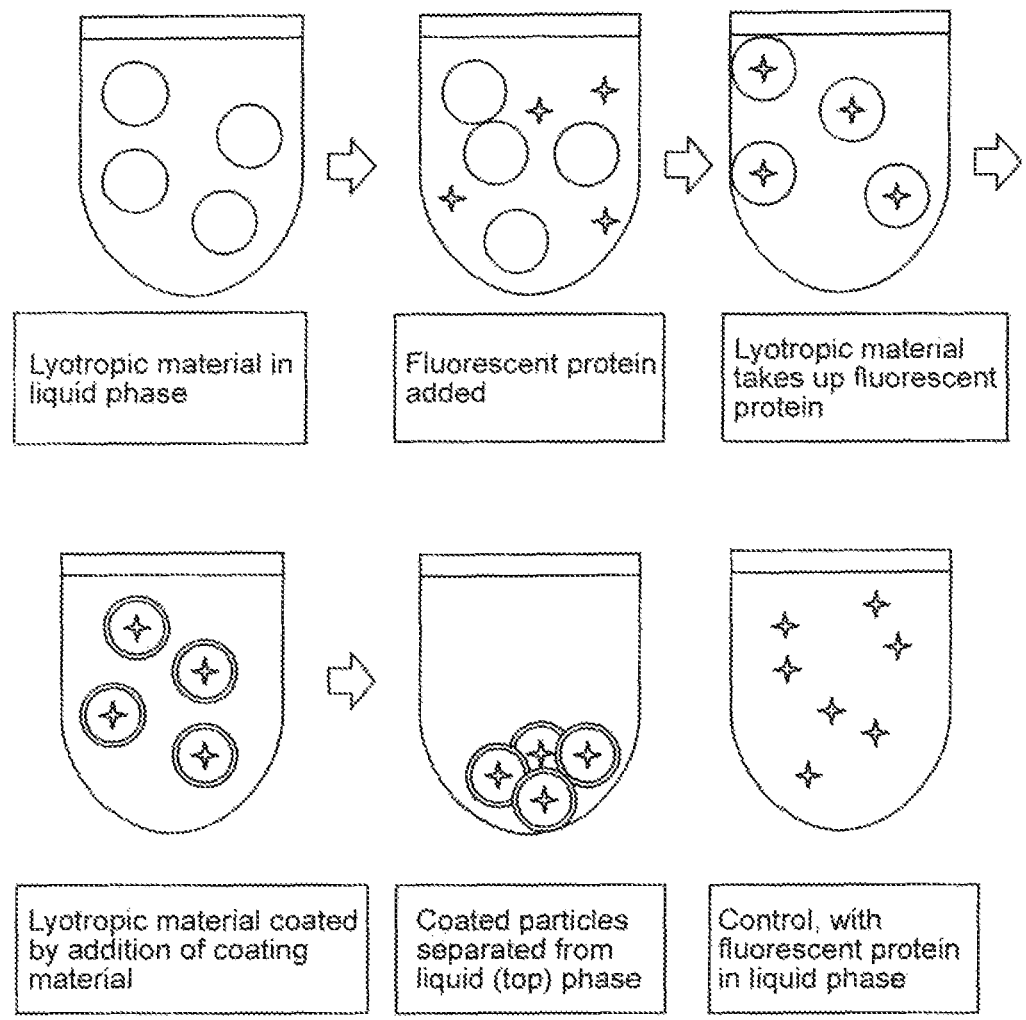
FIG. 6. This figure shows a schematic representation of the procedure and results obtained in the experiment described in Example 12.

A black light photograph of an aliquot of the top phase (in a glass pipette) and an aliquot of the fluorescent control was taken (not shown). The photograph clearly showed that very little fluorescence, indeed an undetectable amount by eye, was visible in the left pipette whilst the control on the right was strongly fluorescent yellow-green. A schematic representation of the experiment and these results are shown in FIG. 6. This Example demonstrates that a protein has been taken up by cubic phase particles prior to coating, after which a solid coating was applied by simple addition of zinc ions, and the coated particles easily collected. As reported in Example 2 above, zinc-NAT coated particles such as these do in fact bind to certain selected substrata.

Example 13

In this Example, cubic phase particles were coated with an energy-absorbing matrix material useable in MALDI and SELDI. The same protocol for making zinc-NAT coated particles was used in this experiment, except that the N-acetyl-tryptophan was replaced by an equimolar amount of Trans-3-indolacrylic acid. The resulting particles were examined by differential interference contrast microscopy and found to be coated by the energy-absorbing matrix material.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A method of preventing non-specific binding during an assay that uses a solid support or substrate, comprising the steps of:
   binding one or more capture molecules to a surface of said support or substrate;
   binding lyotropic liquid or liquid crystal material to said surface of said support or substrate at locations on said surface where capture molecules are not bound, whereby samples exposed to said support or substrate are presented with one or more regions for enabling specific binding said one or more capture molecules and are blocked from non-specific binding to said surface of said support or substrate by said lyotropic liquid or liquid crystal material.

2. The method of claim 1 wherein said step of binding lyotropic liquid or liquid crystal material is performed by depositing said lyotropic liquid or liquid crystal material over said surface of said support or substrate after said step of binding one or more capture molecules to said surface of said support or substrate.

3. The method of claim 1 wherein said lyotropic or liquid crystalline material is bound to said support or substrate in the form of a plurality of particles.

4. The method of claim 3 wherein said particles are coated.

5. The method of claim 3 wherein said particles are uncoated.

6. The method of claim 1 wherein said step of binding said lyotropic or liquid crystalline material to said support or substrate is performed by bonding directly to said support or substrate.

7. The method of claim 6 wherein said bonding is hydrogen bonding.

8. The method of claim 6 wherein said bonding is ionic bonding.

9. The method of claim 1, wherein said lyotropic liquid or liquid crystalline material is cubic phase.

10. The method of claim 3 wherein some or all of said plurality of particles are charged.

11. The method of claim 10 wherein said binding step is achieved using a charge on said particles that are charged to interact with said surface of said support or substrate.

12. The method of claim 5 wherein some or all of said plurality of particles are charged.

13. The method of claim 12 wherein said binding step is achieved using a charge on said particles that are charged to interact with said surface of said support or substrate.

* * * * *